US010086071B2

(12) United States Patent
Yun et al.

(10) Patent No.: US 10,086,071 B2
(45) Date of Patent: Oct. 2, 2018

(54) METHODS OF TREATING A SUBJECT FOR A CONDITION

(71) Applicant: PALO ALTO INVESTORS, Palo Alto, CA (US)

(72) Inventors: Anthony Joonkyoo Yun, Menlo Park, CA (US); Patrick Yuarn-Bor Lee, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 658 days.

(21) Appl. No.: 14/035,814

(22) Filed: Sep. 24, 2013

(65) Prior Publication Data

US 2014/0086872 A1 Mar. 27, 2014

Related U.S. Application Data

(63) Continuation of application No. 10/917,270, filed on Aug. 11, 2004, now Pat. No. 8,569,277.

(51) Int. Cl.
| | |
|---|---|
| *A61K 31/192* | (2006.01) |
| *A61K 39/395* | (2006.01) |
| *A61K 31/573* | (2006.01) |
| *A61K 31/60* | (2006.01) |
| *A61K 38/26* | (2006.01) |
| *A61K 38/49* | (2006.01) |
| *A61K 31/165* | (2006.01) |
| *A61K 31/4178* | (2006.01) |
| *A61K 38/21* | (2006.01) |
| *A61K 38/48* | (2006.01) |

(52) U.S. Cl.
CPC ........ *A61K 39/3955* (2013.01); *A61K 31/165* (2013.01); *A61K 31/192* (2013.01); *A61K 31/4178* (2013.01); *A61K 31/573* (2013.01); *A61K 31/60* (2013.01); *A61K 38/212* (2013.01); *A61K 38/215* (2013.01); *A61K 38/26* (2013.01); *A61K 38/482* (2013.01); *A61K 38/49* (2013.01)

(58) Field of Classification Search
USPC ....................................................... 514/423
See application file for complete search history.

(56) References Cited

U.S. PATENT DOCUMENTS

| | | | |
|---|---|---|---|
| 4,855,315 A * | 8/1989 | Devlin | A61K 31/40 514/422 |
| 5,061,694 A * | 10/1991 | Aberg | A61K 31/40 514/1.9 |
| 5,188,104 A | 2/1993 | Wernicke et al. | |
| 5,215,086 A | 6/1993 | Terry, Jr. et al. | |
| 5,231,988 A | 8/1993 | Wernicke et al. | |
| 5,263,480 A | 11/1993 | Wernicke et al. | |
| 5,269,303 A | 12/1993 | Wernicke et al. | |
| 5,330,615 A | 7/1994 | Rutecki et al. | |
| 5,335,657 A | 8/1994 | Terry, Jr. et al. | |
| 5,529,992 A | 6/1996 | Weber | |
| 5,540,730 A | 7/1996 | Terry, Jr. et al. | |
| 5,571,150 A | 11/1996 | Wernicke et al. | |
| 5,707,400 A | 1/1998 | Terry, Jr. et al. | |
| 5,978,702 A | 11/1999 | Ward et al. | |
| 6,008,210 A | 12/1999 | Weber | |
| 6,253,109 B1 | 6/2001 | Gielen | |
| 6,319,241 B1 | 11/2001 | King et al. | |
| 6,337,997 B1 | 1/2002 | Rise | |
| 6,356,784 B1 | 3/2002 | Lozano et al. | |
| 6,366,813 B1 | 4/2002 | DiLorenzo | |
| 6,410,524 B1 | 6/2002 | Perez et al. | |
| 6,448,280 B1 | 9/2002 | Carey et al. | |
| 6,459,936 B2 | 10/2002 | Fischell et al. | |
| 6,480,743 B1 | 11/2002 | Kirkpatrick et al. | |
| 6,484,059 B2 | 11/2002 | Gielen | |
| 6,526,318 B1 | 2/2003 | Ansarinia | |
| 6,609,025 B2 | 8/2003 | Barrett et al. | |
| 6,653,306 B1 | 11/2003 | Alexander et al. | |
| 2002/0068718 A1 * | 6/2002 | Pierce | A61K 31/728 514/54 |
| 2002/0177882 A1 | 11/2002 | DiLorenzo | |
| 2003/0018367 A1 | 1/2003 | DiLorenzo | |
| 2003/0096789 A1 | 5/2003 | Bissery | |
| 2003/0124174 A1 * | 7/2003 | Galer | A61K 9/7023 424/449 |
| 2003/0144709 A1 | 7/2003 | Zabara et al. | |
| 2003/0190357 A1 | 10/2003 | Marin et al. | |
| 2004/0132703 A1 | 7/2004 | Belanoff | |

OTHER PUBLICATIONS

Barr et al., Am J Cardiol, 1997;79:328-333.*
Andersson and Persson, European Heart Journal, 1994;15 (Suppl C), 52-56.*
Juel et al., Journal of Pain Research, 2017;10:1347-1355.*
Asimakopolous, G., "Systemic Inflammation and Cardiac Surgery: an update" Perfusion (2001) 16(5):353-360 (Abstract Only).
Auckerman et al., "Management of the Acute Migraine Headache" Am. Fam. Physician (2002) 66:2123-30; 2140-1.
Camerer et al. "Tissue factor and factor X-dependent activation of protease-activated receptor 2 by factor VIIa" Proc. Natl. Acad. Sci. USA (2000) 97:5255-5260.
Chu et al., "Successful Long-Term Treatment of Refractory Cushing's Disease with High-Dose Mifepristone (RU 486)" J. Clin. Endocrin. & Metab. (2001) 86:3568-3573.
De Jonge et al. "Activation of coagulation by administration of recombinant factor VIIa elicits interleukin 6 (IL-6) and IL-8 release in healthy human subjects" Clin. Diagn. Lab. Immunol. (2003) 10(3):495-497.
Elenkov et al., "The sympathetic nerve—an integrative interface between two supersystems: the brain and the immune system" Pharmacol. Rev. (2000) 52(4):595-638.

(Continued)

*Primary Examiner* — San Ming R Hui
(74) *Attorney, Agent, or Firm* — Otto C. Guedelhoefer, IV; Bret E. Field; Bozicevic, Field & Francis LLP

(57) ABSTRACT

Methods are provided for treating a subject for at least one condition that includes inflammation, a blood clotting condition and autonomic nervous system dysfunction such as adrenergia, e.g., simultaneously. Also provided are kits for use in practicing the subject methods.

2 Claims, No Drawings

(56) References Cited

OTHER PUBLICATIONS

Elenkov et al., "Modulatory effects of glucocorticoids and catecholamines on human interleukin-12 and interleuklin-10 production: Clinical implications" Proc Assoc. Am. Physicians (1996) 108(5):374-381.

Ferrario et al., "The hypertension-lipid connection: insights into the relation between antiotension II and cholesterol in atherogenesis" Am. J. Med. Sci (2002) 323(1):17-24 (Abstract Only).

Gear et al., Platelet chemokines and chemokine receptors: linking hemostatis, inflammation, and host defense: Microcirculation (2003) 10(3-4):335-350 (Abstract Only).

Hennekens, C.H., "Update on Aspirin in the Treatment and Prevention of Cardiovascular Disease" Am. J. Managed Care (2002) 8(22):S691-S700.

Huskisson, E.C., "Simple Analgesics for Arthritis" British Medical Journal (1974) 4:196-200.

Johnson et al., "Potential mechanisms for a proinflammatory vascular cytokine response to coagulation activation" J. Immunol. (1998) 160(10):5130-5135 (Abstract Only).

Kahn et al., "Protease-activated receptors 1 and 4 mediate activation of human platelets by thrombin" J. Clin. Invest. (1999) 103(6):879-887.

Keller et al., "Infections and endothelial cells" Cardiovasc. Res. (2003) 601(1):40-48.

Kumar et al., "Diabetes and the QT Interval: Time for Debate" B. J. Diabetes Vas. Dis. (2004) 4(3):146-150.

Lande et al., "Increased Platelet and vascular smooth muscle reactivity to low-dose adrenaline infusion in mild essential hypertension" J. Hypertens. (1988) 6(3):219-225 (Abstract Only).

Levi et al., "Infection and inflammation and the coagulation system" Cardiosvasc. Res. (2003) 60(1):26-39.

Lorton et al., "Potential use of drugs that target neural-immune pathways in the treatment of rheumatoid arthritis and other autoimmune diseases" Curr. Drug Targets Inflamm. Allergy (2003) 2(1):1-30 (Abstract Only).

Naldini et al., "Inhibition of interleukin-12 expression by alpha-thrombin in human peripheral blood mononuclear cells: a potential mechanism for modulating Th1/Th2 responses" Br. J. Pharmacol. (2003) 140(5):980-986 (Abstract Only).

Naumann et al., "Botulinum Toxin in the Treatment of Neurological Disorders of the Autonomic Nervous System" Arch. Neurol. (1999) 56:914-916.

Noble et al., "Enoxaparin: A Reappraisal of its Pharmacology and Clinical Applications in the Prevention and Treatment of Thromboembolic Disease" Drugs (1995) 49(3):388-410.

Palermo et al., "Decreased fibrinolytic response to adrenergic stimulation in hypertensive patients" J. Hypertens. (1989) pp. S162-S163 (Abstract Only).

Panina-Borgdinon et al., "Beta2-agonists prevent Th1 development by selective inhibition of interleukin 12" J. Clin. Invest. (1997) 100(6):1513-1519.

Rosenow et al., "Sleep apnoea in endocrine diseases" J. Sleep Res. (1998) 7:3-11.

Savola et al., "Arthropathy induced by beta blockade" Brit. Med. J. (Clin. Res. Ed.) (Oct. 29, 1983) 287 (6401):1256-1257.

Shamsuzzaman et al., "Obstructive Sleep Apnea: Implications for Cardiac and Vascular Disease" JAMA (2003) 290 (14):1906-1914.

Shaw et al., "B cell therapy for rheumatoid arthritis: the rituximab (anti-CD20) experience" Ann. Rheum. Dis. (2003) 62(Suppl. II):ii55-ii59.

Suberville et al., "Regulation of Interleukin-10 production by beta-adrenergic agonists" Eur. J. Immunol. (1996) 26 (11):2601-2605.

Van Der Poll et al., "Epinephrine inhibits tumor necrosis factor-alpha and potentiates interleukin 10 production during human endotoxemia" J. Clin. Invest. (1996) 97(3):713-719.

Von Kanel et al., "Effects of nonspecific Beta-adrenergic stimulation and blockade on bioodcoagulation in hypertension" J. Appl. Physiol. (2003) 94(4):1455-1459.

Von Kanel et al., "Effects of psychological stress and psychiatric disorders on blood coagulation and fibronolysis: a biobehavioral pathway to coronary artery disease?" Psychosom. Med. (2001) 63(4):531-544.

Von Kanel et al. "Effects of sympathetic activation by adrenergic infusions on hemostasis in vivo" Eur. J. Haematol. (2000) 65(6):357-369 (Abstract Only).

Von Kanel et al., "Effect of beta2-adrenergic receptor functioning and increased norepinephrine on the hypercoagulable state with mental stress" Am. Heart J. (2002) 144(1):68-72 (Abstract Only).

* cited by examiner

METHODS OF TREATING A SUBJECT FOR A CONDITION

BACKGROUND OF THE INVENTION

There are a variety of conditions that can affect an individual's health and well-being. The treatment of various conditions that affect the health and well-being of an individual has been around for centuries and in general, the armament of treatment options available to a physician to treat such conditions has increased tremendously, especially in the last century.

However, because of the increase in available treatment options, often times an individual suffering from a variety of different conditions must be administered multiple, different drugs, each intended to treat one of the conditions. For example, many individuals suffering from cardiovascular conditions may be required to adhere to a tedious and exacting schedule of consuming multiple pills throughout a day, where the number of pills may be as much 20 pills a day or more. These types of treatment regimes not only impact an individual's quality of life, but also contribute to rising health care costs. For example, it is estimated that in 2000 health care spending rose to $1.3 trillion in the United States. A large part of this expense is due to the costs of drugs.

As such, there continues to be an interest in the development of new protocols for treating medical conditions.

SUMMARY OF THE INVENTION

Methods are provided for treating a subject for at least one condition. Embodiments include treating a subject for an inflammatory condition, blood clotting condition and autonomic dysfunction simultaneously and include identifying the inflammatory condition, blood clotting condition and autonomic dysfunction in the subject. Embodiments of the subject methods may include one more of the following: administering an effective amount of a single pharmacological agent to a subject chosen from: an anti-inflammatory agent, an anti-blood clotting agent and an autonomic nervous system modulator such as an anti-adrenergic to treat the subject for the identified condition(s); electrically and/or pharmacologically modulating either an inflammatory or blood clotting or autonomic receptor to increase parasympathetic/sympathetic ratio; and modulating one or more enzymes to increase or decrease enzyme activity to increase the parasympathetic/sympathetic ratio.

Embodiments also include treating a subject for an inflammatory condition by identifying the inflammatory condition in the subject and administering an effective amount of at least one of an anti-blood clotting agent and an autonomic nervous system modulator such as an anti-adrenergic agent to the subject, and/or electrically and/or pharmacologically modulating a blood clotting and/or autonomic receptor to increase the parasympathetic/sympathetic ratio; and/or modulating one or more blood clotting pathway enzymes to increase or decrease enzyme activity to increase the parasympathetic/sympathetic ratio.

Embodiments also include treating a subject for a blood clotting condition by identifying the blood clotting condition in the subject and administering an effective amount of at least one of an anti-inflammatory agent and an autonomic nervous system modulator such as an anti-adrenergic agent to the subject, and/or electrically and/or pharmacologically modulating an inflammatory and/or autonomic receptor to increase the parasympathetic/sympathetic ratio, and/or modulating one or more an inflammatory cascade enzyme to increase the parasympathetic/sympathetic ratio, and/or modulating one or more inflammatory pathway enzymes to increase or decrease enzyme activity to increase the parasympathetic/sympathetic ratio.

Embodiments also include treating a subject for autonomic dysfunction by identifying the autonomic dysfunction in the subject and administering an effective amount of at least one of an anti-inflammatory agent and an anti-blood clotting agent, and/or targeting an inflammatory and/or blood clotting receptor to increase the parasympathetic/sympathetic ratio, and/or electrically and/or pharmacologically modulating an inflammatory cascade enzyme to increase the parasympathetic/sympathetic ratio, and/or modulating one or more inflammatory pathway enzymes to increase or decrease enzyme activity to increase the parasympathetic/sympathetic ratio.

Also provided are kits for use in practicing the subject methods.

DETAILED DESCRIPTION OF THE INVENTION

Methods are provided for treating a subject for at least one condition. Embodiments include treating a subject for an inflammatory condition, blood clotting condition and autonomic dysfunction simultaneously and include identifying the inflammation, blood clotting and autonomic dysfunction in the subject. Embodiments of the subject methods may include one more of the following: administering an effective amount of a single pharmacological agent to a subject chosen from: an anti-inflammatory agent, an anti-blood clotting agent and an autonomic nervous system modulator such as an anti-adrenergic to treat the subject for the identified condition(s); electrically and/or pharmacologically modulating either an inflammatory or blood clotting or autonomic receptor to increase parasympathetic/sympathetic ratio; and modulating one or more inflammatory pathway enzymesto increase or decrease enzyme activity to increase the parasympathetic/sympathetic ratio.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

As summarized above, the subject invention provides methods for treating a subject for inflammation and/or blood clotting and/or adrenergia. In further describing the subject invention, representative embodiments of the subject methods are described first in greater detail, followed by a review of various representative applications in which the subject methods may find use. Next, a review of kits for use in the subject methods is provided.

Methods

Embodiments of the subject methods are directed to treating a subject for at least one condition and in many embodiments for two or more conditions, e.g., at the same time. More specifically, methods are provided for treating a subject for inflammation and/or blood clotting and/or autonomic dysfunction (e.g., a low parasympathetic function/sympathetic function ratio in at least a portion of the autonomic nervous system). "Inflammatory condition" broadly refers to conditions caused by proinflammatory cytokines or an inflammatory cytokine cascade. These cytokines include, but are not limited to, tumor necrosis factor (TNF; also known as TNF alha or cachectin), interleukins such as IL-1 or IL-2 or IL-6 or IL-8 or IL-18, interferons such as interferon alpha or interferon beta or interferon gamma, platelet-activating factor (PAF) and macrophage migration inhibitor factor (MIF). By "blood clotting" is meant broadly to include any condition related to the clotting of blood and includes coagulation and/or thrombosis. By "autonomic dysfunction" is meant broadly to include a condition of the autonomic nervous system that manifests as abnormal parasympathetic activity/sympathetic activity ratio, where normal is meant to refer to the parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). Autonomic dysfunction may be characterized by an abnormally high parasympathetic activity/sympathetic activity ratio or an abnormally low parasympathetic activity/sympathetic activity ratio. In certain embodiments, inflammation, blood clotting and autonomic dysfunction may be treated at the same time with the same pharmacological agent, i.e., with a single pharmacological agent, such that separate agents are not needed to treat a subject for these three conditions. Broadly characterized, embodiments of the subject methods include identifying a subject suffering from a condition such as inflammation, blood clotting, autonomic dysfunction, and the like, and treating the subject for the identified condition(s).

The subject methods may be used to treat a variety of blood clotting disorders and/or inflammatory conditions and/or autonomic nervous system dysfunction disorders.

Examples of autonomic dysfunction disorders include, but are not limited to, reflex sympathetic dystrophy, migraines, bladder dysfunction, hepatorenal syndrome, pulmonary renal syndrome, shy draggers, multi-symptom atrophy, cardiogenic pulmonary edema, cerebral vascular vasospasm, migranes, pregnancy-related arrhythmias, transplant-related tachycardia, QT interval prolongation, arterial vasospasm, fatal arrhythmias, coronary vasospasm, sick sinus syndrome, bradycardia, tachycardia, arrhythmias, paroxysmal supraventricular tachycardia, and the like.

Examples of inflammatory conditions include, but are not limited to, neurodegenerative conditions including neurodegenerative diseases, e.g., Alzheimer's Disease, Pick's Disease, Parkinson's Disease, dementia, delirium, amyotrophic lateral sclerosis, and the like; neuroinflammatory conditions including neuroinflammatory diseases, e.g., viral meningitis, viral encephalitis, fungal meningitis, fungal encephalitis, multiple sclerosis, charcot joints, schizophrenia, myasthenia gravis, and the like; orthopedic inflammatory conditions including orthopedic inflammatory diseases, e.g., osteoarthritis, inflammatory arthritis, regional idiopathic osteoporosis, reflex sympathetic dystrophy, Paget's disease, osteoporosis, antigen-induced arthritis, juvenile chronic arthritis, and the like; lymphoproliferative conditions including lymphoproliferative diseases, e.g., lymphoma, lymphoproliferative disease, Hodgkin's disease, inflammatory pseudomotor of the liver, and the like; autoimmune conditions including automimmune diseases, e.g., Graves disease, raynaud's, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, Reiter's disease, lupus, multiple sclerosis, rheumatoid arthritis, and the like; infectious diseases, e.g., sepsis, viral and fungal infections, diseases of wound healing, tuberculosis, infection, AIDS, human immunodeficiency virus, and the like; pulmonary conditions including pulmonary diseases, e.g., tachypnea, fibrotic lung diseases such as cystic fibrosis and the like, interstitial lung disease, desquamative interstitial pneumonitis, non-specific interstitial pneumonitis, intrapulmonary shunts; lymphocytic interstitial pneumonitis, usual interstitial pneumonitis, idiopathic pulmonary fibrosis, aspiration, asphyxiation, pneumothorax, right-to-left shunts, left-to-right shunts, respiratory failure, and the like; transplant-related conditions such as transplant related side effects such as transplant rejection, transplant related renal failure, transplant related bowel dysmotility, transplant-related hyperreninemia, and the like; gastrointestinal conditions including gastrointestinal diseases, e.g., hepatitis, xerostomia, bowel mobility, peptic ulcer disease, constipation, ileus, irritable bowel syndrome, post-operative bowel dysmotility, inflammatory bowel disease, typhilitis, cholelethiasis, cholestasis, fecal incontinence, cyclic vomiting syndrome, and the like; endocrine conditions including endocrine diseases, e.g., hypothyroidism, hyperglycemia, diabetes, obesity, syndrome X, insulin resistance, polycystic ovarian syndrome ("PCOS"), and the like; genitourinary conditions including genitourinary diseases, e.g., renal failure, erectile dysfunction, hyperreninemia, incontinence, arousal disorder, menopausal mood disorder, premenstrual mood disorder, renal tubular acidosis, pulmonary renal syndrome, and the like; skin conditions including skin diseases, e.g., wrinkles, cutaneous vasculitis, psoriasis, rash; and the like; aging associated conditions including aging associated diseases, e.g., age related inflammation conditions, cancer, aging, and the like; neurologic conditions including neurologic diseases such as epilepsy, depression, schizophrenia, seizures, stroke, insomnia, cerebral vascular accident, transient ischemic attacks, stress, bipolar disorder, concussions, post-concussive syndrome, central sleep apnea, obstructive sleep apnea, sleep disorders, headaches including chronic headaches, acute disseminated encephalomyelitis ("ADEM"), and the like; pediatric conditions, including pediatric diseases, e.g., respiratory distress syndrome, sudden infant death syndrome, hirschsprung disease, bronchopulmonary dysplasia, congenital megacolon, ananglionosis, juvenile rheumatoid arthritis, juvenile chronic arthritis, and the like; Th-2 dominant conditions including Th-2 dominant diseases, e.g., typhilitis, osteoporosis, lymphoma, myasthenia gravis, lupus, and the like; conditions, including diseases, that cause hypoxia, hypercarbia, hypercapnia, acidosis, acidemia, such as obstructive sleep apnea, chronic obstructive pulmonary disease ("COPD"), emphysema, any chronic lung disease that causes acidosis, acute pulmonary embolism, sudden adult death syndrome ("SADS"), chronic pulmonary embolism, pleural effusion, non-cardiogenic pulmonary edema, acute respiratory distress syndrome (ARDS), neurogenic edema, hypercapnia, acidemia, asthma, renal tubular, asthma, acidosis, chronic lung diseases that cause hypoxia, hypercarbia or hypercapnia, and the like; OB-GYN conditions including OB-GYN diseases, e.g., amniotic fluid embolism, menopausal mood disorders, premenstrual mood disorders, fetal stress syndrome, fetal hypoxia, amniotic fluid embolism, gestational diabetes, pre-term labor, cervical incompetence, fetal distress, peri-partum maternal mortality, peripartum cardiomyopathy, labor complications, premenstrual syndrome, dysmenorrheal, endometriosis, infertility, early pregnancy loss, spontaneous abortion, subfertility, failure of implantation, amenorrhea, luteal insufficiency, dysmenorrheal, pelvic pain and the like; menstrual related disorders, e.g., pelvic pain, dysmenorrheal, nausea, and the like; peripartum and pregnancy related conditions, e.g., peripartum cardiomyopathy, and the like; post-operative recovery conditions such as post-operative pain, post operative ileus, post-operative fever, post-operative nausea, and the like; post-procedural recovery conditions such as post-procedural pain, post procedural ileus, post-procedural fever, post-procedural nausea, and the like; chronic pain; trauma; hospitalization; glaucoma; male infertility; disorders of thermoregulation; respiratory sinus arrhythmia; VQ mismatch; fibromyalgia; and the like.

Examples of blood clotting conditions include, but are not limited to, cardiovascular conditions such as atherosclerosis, coronary artery disease, hypertension, hyperlipidemia, eclampsia, pre-eclampsia, cardiomyopathy, volume retention, congestive heart failure, aortic dissection, aortic aneurysm, arterial aneurysm, myocardial infarction, ischemia, sudden adult death syndrome, acute coronary syndromes, thromboembolic disease, deep vein thrombosis, coagulopathy, disseminated intravascular coagulation, mesenteric ischemia, syncope, venous thrombosis, arterial thrombosis, malignant hypertension, primary pulmonary hypertension, secondary pulmonary hypertension, raynaud's, and the like.

Identifying Conditions to be Treated

The first step in the subject methods is to identify the condition(s) experienced by a subject or least identify conditions at least suspected of being present or for which a subject may be susceptible (i.e., the subject methods may be employed prophylactically to prevent a subject from experiencing a condition). Any suitable technique may be employed to identify conditions and include qualitative and quantitative methods. A variety of different methods for detecting inflammation and/or blood clotting and/or adrenergia are known to those of skill in the art.

For example, methods for identifying an inflammatory condition (e.g., for assessing the site(s) and extent of the inflammatory process) are known in the art and include, but are not limited to, conventional x-ray techniques, computerized axial tomographic scanning (CAT scanning), a variety of radionuclide scans (Sutton, A Textbook of Radiology and Imaging, 3rd Ed., Churchill Livingston, 1980; Clinical Nuclear Medicine, Maysey et al., ed., W. B. Sanders, 1983.) and the like. Examples of radionuclide scans which have been utilized include: $^{67}$Gallium, which when injected into an animal or a human binds to the plasma protein transferring and tends to localize at sites of chronic inflammation; $^{111}$Indium labeled endogenous granulocytes, which when re-injected into the host will tend to accumulate at the site of inflammation; radiolabeled chelates which pass into the extracellular fluid and can possibly then accumulate at such sites of fluid accumulation as those associated with inflammation; and thallium scans or so-called first pass radionuclide angiograms employed to assess areas of increased blood flow. Techniques analogous to those described in U.S. Pat. No. 5,363,846, the disclosure of which is herein incorporated by reference, may also be used to identify inflammation. Other tests known in the art include Erythrocyte Sedimentation Rate (ESR) tests and C Reactive Protein ("CRP") tests.

Methods for identifying a blood clotting condition (e.g., thrombosis and/or coagulation) are also well known in the art and include, but are not limited to, methods described in U.S. Pat. Nos. 5,849,507; 5,525,477; and 3,486,981, the disclosures of which are herein incorporated by reference. In certain embodiments, automated, computer-controlled instruments such as coagulometers and the like may be employed. Various imaging apparatuses may also be employed, e.g., ultrasounds and the like, for example, to diagnose deep vein thrombosis.

Various methods for identifying autonomic activity and autonomic dysfunction are also known. For example, measurements of heart rate variability ("HRV") may be used as an indicator of autonomic dysfunction, as well as levels of T helper cells (Th1 and/or Th2), and the like, e.g., as an indicator of the parasympathetic activity/sympathetic activity ratio.

Treating the Subject for the Identified Condition(s)

Once it is determined that a subject is in need of treatment for at least one condition such as at least one of inflammation, blood clotting and autonomic dysfunction, the subject may then be treated for the identified condition(s) in accordance with the subject invention. Embodiments of the subject invention include treating a subject for any one of, inflammation, blood clotting and autonomic dysfunction by electrically and/or pharmacologically modulating an inflammatory or blood clotting or autonomic receptor (e.g., stimulate or inhibit a receptor, e.g., block a receptor) to increase parasympathetic/sympathetic ratio (e.g., to effect binding affinity and/or signal transduction), and/or by targeting or modulating one or more enzymes, such as inflammatory pathway enzymes, to increase or decrease enzyme activity to increase the parasympathetic/sympathetic ratio.

Embodiments of the subject invention include treating a subject for any one of, inflammation, blood clotting and autonomic dysfunction by administering an effective amount of one of: an anti-inflammatory agent, anti-blood clotting agent and an autonomic system modulator such as an anti-adrenergic agent to treat one of, two of, or all three of the inflammation, blood clotting an autonomic dysfunction. By "anti-inflammatory agent" and analogous terms is meant an agent that counteracts or suppresses the inflammatory process. By "anti-blood clotting agent" and analogous terms is meant broadly to include anti-thrombotics and anti-coagulants where such agents act to prevent or interfere with the coagulation pathways and/or the formation of thrombi, but in any event prevent or interfere with a body's ability to promote or form blood clots. By "autonomic nervous system modulator" and analogous terms (e.g., anti-adrenergic, anti-sympathetic, and the like) is meant an agent that is capable of modulating at least a portion of the autonomic nervous system. An autonomic nervous system modulator may modulate at least a portion of the autonomic nervous system in a number of ways, e.g., may increase parasympathetic activity, may decrease parasympathetic activity, may increase sympathetic activity, may decrease sympathetic activity. An example of an autonomic nervous system modulator is an anti-adrenergic agent. By "anti-adrenergic" and analogous terms is meant an agent that blocks the effects of the sympathetic nervous system, e.g., by blocking receptors or decreasing the release of NE/EPI.

Accordingly, embodiments of the subject invention provide a manner whereby one, two or all three conditions may be treated by using a single pharmacological agent. For example, if it is determined that a subject has one or more of an inflammatory condition, a blood clotting condition, and/or an autonomic dysfunction condition such as adrenergia and it is determined that the subject requires treatment for the identified condition(s), an effective amount of an anti-inflammatory agent may be administered to treat the subject for the inflammatory condition, blood clotting condition and/or autonomic dysfunction condition such as adrenergia. In certain embodiments, if it is determined that a subject has one or more of an inflammatory condition, a blood clotting condition, and an autonomic dysfunction condition such as adrenergia and requires treatment thereof, an effective amount of an anti-blood clotting agent may be administered to treat the subject for the inflammatory condition, blood clotting condition and/or autonomic dysfunction condition such as adrenergia. In certain embodiments, if it is determined that a subject has one or more of an inflammatory condition, a blood clotting condition, and an autonomic dysfunction condition such as adrenergia and requires treatment thereof, an effective amount of an autonomic nervous system modulator such as an anti-adrenergic agent or the like may be administered to treat the subject for the inflammatory condition, blood clotting condition and/or autonomic dysfunction condition such as adrenergia. In this manner, the number of different medications required to treat a subject for more than one type of condition is reduced.

In certain embodiments, if it is determined that a subject has one or more of an inflammatory condition, a blood clotting condition, and an autonomic dysfunction condition such as adrenergia and requires treatment thereof, receptors may be modulated in a manner that modulated at least a portion of the autonomic nervous system, e.g., increases the parasympathetic activity/sympathetic activity ratio to treat the subject for the inflammatory condition, blood clotting condition and/or autonomic dysfunction condition such as adrenergia. As will be known to those of skill in the art, receptors may be modulated in a manner that, for example, effects signal transduction and/or ligand binding affinity.

In certain embodiments, if it is determined that a subject has one or more of an inflammatory condition, a blood clotting condition, and an autonomic dysfunction condition such as adrenergia and requires treatment thereof, inflammatory pathway enzymes may be targeted or modulated to increase or decrease enzyme activity to increase the parasympathetic/sympathetic ratio.

In certain embodiments, it may be determined that a subject is only experiencing one or two of the conditions. In such embodiments, any one of the conditions may be treated with any one of an anti-inflammatory; anti-blood clotting and autonomic nervous system modulator such as an anti-adrenergic agent. Such may be advantageous for a variety of reasons, e.g., drug availability, drug cost, etc.

Accordingly, embodiments include treating a subject for an inflammatory condition without administering an anti-inflammatory agent to the subject. Such embodiments may include identifying a subject suffering from an inflammatory condition and administering an effective amount of at least one of an anti-blood clotting agent and an autonomic nervous system modulator such as an anti-adrenergic agent to the subject to treat the subject for the inflammatory condition. In certain embodiments, a subject may be treated for an inflammatory condition by modulating at least a portion of the autonomic nervous system to increase the parasympathetic activity/sympathetic activity ratio in a manner effective to treat the subject for the inflammation.

Embodiments of the subject invention also include treating a subject for an undesirable blood clotting condition (e.g., coagulation and/or thrombosis) without administering an anti-blood clotting agent to the subject. Such embodiments may include identifying a subject suffering from a blood clotting condition and administering an effective amount of at least one of an anti-inflammatory agent and an autonomic nervous system modulator such as an anti-adrenergic agent to the subject to treat the subject for the blood clotting condition. In certain embodiments, a subject may be treated for a blood clotting condition by modulating at least a portion of the autonomic nervous system to increase the parasympathetic activity/sympathetic activity ratio in a manner effective to treat the subject for the blood clotting condition.

Embodiments of the subject invention also include treating a subject for an autonomic dysfunction condition such as adrenergia without administering an autonomic nervous system modulator such as an anti-adrenergic agent to the subject. Such embodiments may include identifying a subject suffering from an autonomic dysfunction condition such as suffering from adrenergia and administering an effective amount of at least one of an autonomic nervous system modulator such as an anti-inflammatory agent and an anti-blood clotting agent to the subject to treat the subject for the autonomic dysfunction condition such as adrenergia.

As described above, embodiments include treating a subject for a condition such as an inflammatory condition and/or a blood clotting condition and/or autonomic dysfunction condition such as an adrenergic condition by administering an effective amount of a pharmacological agent to treat the subject for the identified conditions or for the conditions at least suspected of being present. In further describing autonomic dysfunction, an adrenergic condition is described as an exemplary condition, where such description is in no way intended to limit the scope of the invention. An anti-adrenergic is described as an exemplary autonomic nervous system modulator where such description is in no way intended to limit the scope of the invention. Accordingly, one or more pharmacological agents may be employed to treat a subject for inflammation, blood clotting and adrenergia where in many embodiments all three conditions are treated at the same time with a single pharmacological agent. As noted above, pharmacological agents of interest include, but are not limited to, anti-inflammatory agents, anti-blood clotting agents and anti-adrenergic agents.

According to embodiments of the subject invention, pharmacological modulation may be accomplished by at least administering an effective amount of at least one pharmacological agent to a subject to treat the subject for at least one condition and in many embodiments a plurality of different conditions. That is, embodiments of the subject methods include administering an effective amount, i.e., a therapeutically effective amount, of one or more pharmacological agents to a subject to treat the subject for an identified (or suspected) condition or plurality of conditions such as inflammation and/or thrombosis and/or adrenergia. By "effective amount" and analogous terms is meant an amount effective to facilitate a desired therapeutic effect, e.g., a desired reduction in severity and/or frequency of one or more identified (or suspected) conditions such as inflammation and/or blood clotting and/or adrenergia, for a given period of time. The effective amount will vary with the age and physical condition of the subject, type and severity of the condition being treated, the duration of the treatment, the nature of any concurrent treatment, the pharmaceutically acceptable carrier used if any, and analogous factors within the knowledge and expertise of those skilled in the art.

The effective amount of a given pharmacological agent may vary somewhat from subject to subject, and may depend upon factors such as, but not limited to, the age and condition of the subject, the form of the pharmacological agent, the route and method of delivery, etc., as noted above. Such dosages may be determined in accordance with routine pharmacological procedures known to those skilled in the art. For example, a pharmacological agent and/or adjuvants may be administered to a subject in a single oral dose, one time a day or more for days, weeks, months, years, even as long as a subject's lifetime. For example, embodiments may include administering a given pharmacological agent one time a day over a prolonged period of time, e.g., over about 1 week, e.g., over about 1-3 months, e.g., about 3 months to about 3 years or more, e.g., orally or with a medical infusion pump or similar device designed for delivery of a substance over a prolonged period. The frequency of administration of a pharmacological agent may vary depending, e.g., on one or more of the factors described above. For example, the frequency of administration may range from about 1 time per day to multiple times per day, e.g., about 2 times or more per day or as necessary to treat or otherwise control or manage a condition, e.g., to treat a subject for inflammation and blood clotting and adrenergia. The duration of therapy depends on the type of condition being treated and may range from as short as about 24 hours to as long as the life of the subject. By "adjuvants" is meant a compound that, when used in combination with the one or more pharmacological agent compounds and/or compositions, augments or otherwise alters or modifies the resultant pharmacological and/or physiological responses.

Embodiments may include daily discrete or continuous unit doses wherein the total number of daily units may be equal to the total number of days of a given week, month, or the like, e.g., in the form of a pack. For example, embodiments may include daily discrete or continuous unit doses wherein the total number of daily units may be equal to the total number of days of a week or month, e.g., in the form of a monthly pack.

Embodiments also include pharmaceutical compositions in unit dosage forms that are useful in treating conditions by modulating at least a portion of a subject's autonomic nervous system and which contain at least two different pharmacological agents. In certain embodiments, a single unit dosage form may include pharmacological agents of different classes or types. For example, a single drug administration entity may include two or more different classes of pharmacological agents such as an anti-inflammatory agent and an anti-adrenergic agent or an anti-inflammatory agent and an anti-blood clotting agent or an anti-blood clotting agent and an anti-adrenergic agent. For example, a single tablet, capsule, dragee, trocheem suppository, syringe, and the like, combining two or more pharmacological agents of different classes, e.g., a single drug administration entity may include an anti-inflammatory agent and an anti-adrenergic agent or an anti-inflammatory agent and an anti-blood clotting agent or an anti-blood clotting agent and an anti-adrenergic agent, would be a unit dosage form. Such compositions may be included as part of a therapeutic package in which one or more unit doses are placed in a finished pharmaceutical container. The actual amounts of each anti-inflammatory agent and/or anti-adrenergic agent and/or anti-blood clotting agent will vary according to the specific compositions being utilized, the particular compositions formulated, the mode of application, the particular route of administration, and the like. Dosages for a given subject can be determined using conventional considerations, e.g., by customary comparison of the differential activities of the subject compositions and of a known agent, or by means of an appropriate, conventional pharmacological protocol.

Depending on the particular pharmacological agent administered to a subject, whether an anti-inflammatory agent, anti-blood clotting agent or anti-adrenergic agent, the pharmacological agent may be administered to a subject using any convenient means capable of resulting in the treatment of at least the condition(s) identified. Thus, the at least one pharmacological agent may be incorporated into a variety of formulations for therapeutic administration. More particularly, the active agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the particular pharmacological agent and other optional ingredients of the subject pharmacological agent compositions in that a pharmaceutically acceptable carrier may be combined with the pharmacological agent without eliminating the biological or therapeutically effective activity of the pharmacological agent, and is suitable for use in subjects as provided herein without undue adverse side effects (such as toxicity, irritation, allergic response, and death). Side effects are "undue" when their risk outweighs the benefit provided by the pharmacological agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agent employed in the subject methods may be formulated into preparations in solid, semi-solid (e.g., gel and the like), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, a given pharmacological agent may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

As noted above, embodiments may include pharmaceutical formulations (pharmaceutical anti-inflammatory formulations, pharmaceutical anti-blood clotting formulations and pharmaceutical anti-adrenergic formulations) for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological formulations suitable for oral administration in accordance with the subject invention may be present in discrete units, such as capsules, cachets, lozenges, tablets, and the like, each containing a predetermined amount of the active pharmacological agent, as a powder or granules, as a solution or a suspension in a pharmacological formulation, and the like, and may be prepared by any suitable method of pharmacy which includes, but is not limited to, bringing into association the active pharmacological agent and a suitable carrier (which may contain one or more optional ingredients as noted above). For example, pharmacological formulations for use with the subject invention may be prepared by uniformly and intimately admixing the active pharmacological agent with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

A pharmacological anti-inflammatory, anti-blood clotting or anti-adrenergic agent of this invention may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include a pharmacological agent made into suppositories by mixing with a variety of bases such as emulsifying bases or water-soluble bases.

A pharmacological anti-inflammatory, anti-blood clotting or anti-adrenergic agent used in the practice of the subject methods may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include a pharmacological anti-inflammatory, anti-blood clotting or anti-adrenergic agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, a pharmacological anti-inflammatory, anti-thrombotic or anti-adrenergic agent may be utilized in aerosol formulation or an analogous formulation to be administered via inhalation or analogous means. The pharmacological agent employed in the practice of the present invention may be formulated into pressurized acceptable propellants such as dichlorodifluoromethane, propane, nitrogen and the like.

A pharmacological anti-inflammatory, anti-blood clotting or anti-adrenergic agent employed in the subject methods may be delivered transdermally, by a topical route, formulated as applicator sticks, solutions, suspensions, emulsions, gels, creams, ointments, pastes, jellies, paints, powders, and aerosols. For example, embodiments may include a pharmacological agent in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agents are retained. The base or matrix layer may be operatively associated with a support or backing. Pharmacological formulations suitable for transdermal administration may also be delivered by iontophoresis and may take the form of an optionally buffered aqueous solution of the pharmacological compound. Suitable formulations may include citrate or bis/tris buffer (pH 6) or ethanol/water and contain a suitable amount of active ingredient.

A pharmacological anti-inflammatory, anti-blood clotting or anti-adrenergic agent of the invention may also be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

A pharmaceutical formulation employed in the subject methods may be provided as a salt and may be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

Pharmacological formulations employed in the subject invention may be useful for parenteral administration, such as intravenous ("IV") administration, intramuscular ("IM"), subcutaneous ("SC" or "SQ"), mucosal. The formulations for administration may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological formulations suitable for parenteral administration may include sterile aqueous and non-aqueous injection solutions of one or more active pharmacological agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

In certain embodiments, a pharmacological anti-inflammatory, anti-blood clotting or anti-adrenergic agent employed in the subject methods may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include a pharmacological agent administered as liposomal formulations of the pharmacological agent. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

Embodiments of the pharmacological anti-inflammatory, anti-blood clotting or anti-adrenergic agent employed in the practice of the subject invention may include pharmaceutical compositions that may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological anti-inflammatory, anti-blood clotting or anti-adrenergic agents, other additives such as pH-adjusting additives may be added to provide a pharmacological composition. In particular, useful pH-adjusting agents that may be used include acids, such as hydrochloric acid, bases or buffers, such as sodium lactate, sodium acetate, sodium phosphate, sodium citrate, sodium borate, or sodium gluconate. Furthermore, pharmacological compositions may, though not always, contain microbial preservatives. Microbial preservatives that may be employed include, but are not limited to, methylparaben, propylparaben, and benzyl alcohol. The microbial preservative may be employed when the pharmacological formulation is placed in a vial designed for multidose use. Pharmaceutical compositions for use in practicing the subject methods may be lyophilized using techniques well known in the art.

Pharmaceutically acceptable excipients, such as vehicles, adjuvants, carriers or diluents, that may be employed in the subject invention are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of a pharmacological agent such as an anti-inflammatory, anti-blood clotting, anti-adrenergic, or the like, using a pharmacological delivery device such as, but not limited to, pumps (implantable or external devices and combinations of both (e.g., certain components are implantable and others may be external to the body such as controls for the implantable components), epidural injectors, syringes or other injection apparatus, catheter and/or reservoir operatively associated with a catheter, etc. For example, in certain embodiments a delivery device employed to deliver an anti-inflammatory, anti-blood clotting, anti-adrenergic, or the like to a subject may be a pump, syringe, catheter or reservoir operably associated with a connecting device such as a catheter, tubing, or the like. Containers suitable for delivery of a pharmacological agent to a pharmacological agent administration device include instruments of containment that may be used to deliver, place, attach, and/or insert the pharmacological agent into the delivery device for administration of the pharmacological agent to a subject and include, but are not limited to, vials, ampules, tubes, capsules, bottles, syringes and bags. Embodiments may also include administration of a pharmacological agent via a biodegradable implant drug delivery device. Such may be accomplished by employing syringes to deposit such a biodegradable delivery device under the skin of a subject. The implants degrade completely, so that removal is not necessary.

Embodiments may include employing an electrode to deliver a pharmacological anti-inflammatory, anti-blood clotting or anti-adrenergic agent to a subject. For example, an electrode may be used that has a small port at its tip which is connected to a reservoir or pump containing a pharmacological agent. The pharmacological agent delivery electrode may be implanted using any suitable technique such as surgical cut down, laproscopy, endoscopy, percutaneous procedure, and the like. In certain embodiments a reservoir or pump may also be implanted in the subject's body. The pharmacological agent delivery electrode, or other analogous device, may be controllable such that the amount of pharmacological agent delivered, the rate at which the pharmacological agent may be delivered, and the time period over which the pharmacological agent may be delivered, etc., may be controllable and may be adjusted.

In certain embodiments, the pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological formulations include, but are not limited to, formulations that include one or more active pharmacological agents and physiological saline solution (optionally including other typical ingredients such as other active agents and buffers).

As noted above, in pharmaceutical dosage forms, a given anti-inflammatory, anti-blood clotting or anti-adrenergic agent may be administered alone or with or in appropriate association, as well as in combination, with other pharmaceutically active compounds. As used herein, "administered with" means that a given pharmacological agent and at least one other adjuvant (including one or more other different pharmacological agents) are administered at times sufficiently close that the results observed are indistinguishable from those achieved when the pharmacological agent and at least one other adjuvant are administered at the same point in time. The pharmacological agent and at least one other adjuvant (including one or more other different pharmacological agents) may be administered simultaneously (i.e., concurrently) or sequentially. Simultaneous administration may be carried out by mixing a given pharmacological agent and at least one other adjuvant (including one or more other different pharmacological agents) prior to administration, or by administering a given pharmacological agent and at least one other adjuvant (including one or more other different pharmacological agents) at the same point in time. Such administration may be at different anatomic sites or using different routes of administration. The phrases "concurrent administration," "administration in combination," "simultaneous administration" or "administered simultaneously" may also be used interchangeably and mean that a given pharmacological agent and at least one other adjuvant a (including one or more other different pharmacological agents) are administered at the same point in time or immediately following one another. In the latter case, the pharmacological agent and at least one other adjuvant (including one or more other different pharmacological agents) are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant (including one or more other different pharmacological agents), which may result in a synergistic effect or a separate effect. The methods and excipients described herein are merely exemplary and are in no way limiting.

For example, a subject identified as having thrombosis may be treated for the identified thrombosis with the simultaneous administration of an anti-inflammatory agent and an anti-adrenergic agent; a subject identified as having inflammation may be treated for the inflammation with the simultaneous administration of an anti-blood clotting agent and an anti-adrenergic; a subject identified as having adrenergia may be treated for the adrenergia with the simultaneous administration of an anti-blood clotting agent and an anti-inflammatory agent. Embodiments may include treating a subject for two or more identified conditions such as two or more of an inflammatory condition, a blood clotting condition and an adrenergic condition by the simultaneous administration any combination of two or more of an anti-blood clotting agent, anti-inflammatory agent and anti-adrenergic agent. A subject identified as having an inflammatory condition, a blood clotting condition and an adrenergic condition may be treated for the three identified conditions with the simultaneous administration of an anti-thrombotic agent and an anti-inflammatory agent, or an anti-blood clotting agent and an anti-adrenergic, or an anti-inflammatory agent and anti-adrenergic agent.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent such as a predetermined amount of an anti-inflammatory agent, anti-blood clotting agent, anti-adrenergic agent, or the like. Similarly, unit dosage forms for injection or intravenous or other suitable administration route may include a pharmacological agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent(s) calculated in an amount sufficient to produce the desired effect in association with a pharmaceutically acceptable diluent, carrier or vehicle. The specifications for the unit dosage forms of a given pharmacological agent employed in the practice of the present invention depend on, for example, the particular pharmacological agent employed and the effect to be achieved, the pharmacodynamics associated with the particular pharmacological agent in the subject, etc.

As noted above, those of skill in the art will readily appreciate that dose levels may vary as a function of the specific pharmacological agent, the nature of the delivery vehicle, and the like. Dosages for a given pharmacological agent are readily determinable by those of skill in the art by a variety of means. Exemplary dosage levels are provided herein and are not to be construed to limit the scope of the invention in any manner.

A wide variety of different anti-inflammatory, anti-blood clotting and anti-adrenergic agents may be employed in the practice of the subject methods, where the particular anti-inflammatory, anti-blood clotting or anti-adrenergic agent or combination of agents employed will depend on, e.g., the subject being treated, the condition(s) being treated, duration of treatment, whether it is desired to increase activity in the parasympathetic system and/or increase activity in the sympathetic system and/or decrease activity in the sympathetic system and/or decrease activity in the parasympathetic system, etc. Representative pharmacological agents (and analogs, derivatives and salts thereof) include, but are not limited to, one of more of the following exemplary agents. It is to be understood that the subject invention includes analogues, derivatives and salts of the described agents that are now known or to be discovered.

Anti-blood clotting agents including anti-coagulants, anti-platelet agents, and anti-thrombotics may be employed in the practice of the subject invention, including, but not limited to one or more of: triclopidone, clopidogrel, GP IIb/IIIa receptor antagonists, acetylsalicylic acid (ASPIRIN); ximelagatran (EXANTA); hirulog (BIVALIRIDIN); abciximab (REOPRO); dipridamole (AGGRENOX); anagrlide (AGRILYN); clopiogrel (PLAVIX); dipridamole (PERSANTINE); eptifabatide (INTEGRILIN); ticlopidine (TICLID); tirofibam (AGGRASTAT); ardeparin (NORMIFLO); dalteparin (FRAGMIN); dnaparoid (ORGARIN); enoxaparin (LOVENOX); lepiudin (REFLUDAN); heparin; warfarin; alteplase (ACTIVASE), t-PA); reteplase (RETEVASE); streptokinase; urokinase; aminocaproic acid (AMICAR); cilostazol (PLETAL); pentoxifylline (TRENTAL); and the like.

anti-inflammatory agents, including, but not limited to: steroids; non steroidal anti-inflammatory agents (NSAIDs); glucocorticoid receptor blockers (e.g., mifepristone, and the like); immunomodulators (e.g., Interferon Alfa-2A (Roferon-A), Interferon Alfa-2b (Intron-A), Interferon Alfa-2b and Ribavirin combo Pack (Rebetron), Interferon Alfa-N3 (Alferon N), Interferon Beta-1A (Avonex), Interferon Beta-1B (Betaseron), Interferon Gamma, and the like; immunoregulatory antibodies that bind to or reacts with an antigen such as CD4, gp39, B7, CD19, CD20, CD22, CD401, CD40, CD40L and CD23 antigens, rituximab, any chemical or radiopharmaceutical linked or conjugated to antibodies that bind to or reacts with an antigen selected from the group consisting of CD4, gp39, B7, CD19, CD20, CD22, CD401, CD40, CD40L and CD23 antigens; dehydroepiandrosterone (DHEA); antihistamines (e.g., Actifed (Triprolidine) PBZ (Tripelenamine) Allegra (Fexofenadine) Periactin (Cyproheptadine) Antivert or Bonine (Meclizine) Phenergan (Promethazine) Astelin (dispensed as a Nose Spray) Polyhistine (Phenyltoloxamine) Atarax (Hydroxyzine) Seldane (Terfenadine) Benadryl (Diphenhydramine) Semprex (Acrivastine) Bromfed (Brompheneramine) Tavist (Clemastine) Chlortrimeton (Chlorpheniramine) Unisom (Doxylamine) Claritin (Loratidine) Zyrtec (Cetirizine) Dramamine (Dimenhydrinate), and the like).

Autonomic nervous system modulators such as anti-adrenergic agents may be employed in the practice of the subject invention, including, but not limited to one or more of: beta-blockers (e.g., atenolol (e.g., as sold under the brand names Tenormin), betaxolol (e.g., as sold under the brand name Kerlone), bisoprolol (e.g., as sold under the brand name Zebeta), carvedilol (e.g., as sold under the brand name Coreg), esmolol (e.g., as sold under the brand name Brevibloc), labetalol (e.g., as sold under the brand name Normodyne), metoprolol (e.g., as sold under the brand name Lopressor), nadolol (e.g., as sold under the brand name Corgard), pindolol (e.g., as sold under the brand name Visken), propranolol (e.g., as sold under the brand name Inderal), sotalol (e.g., as sold under the brand name Betapace), timolol (e.g., as sold under the brand name Blocadren), carvedilol, and the like); aldosterone antagonists (e.g., spironolactone, eplerenone, and the like); angiotensin II receptor blockades (e.g., candeartan (e.g., available under the brand name Altacand), eprosarten mesylate (e.g., available under the brand name Tevetan), irbesartan (e.g., available under the brand name Avapro), losartan (e.g., available under the brand name Cozaar), etelmisartin (e.g., available under the brand name Micardis), valsartan (e.g., available under the brand name Diovan), and the like); angiotensin converting enzyme ("ACE") inhibitors (e.g., benazapril (e.g., available under the brand name Lotensin), captopril (e.g., available under the brand name Capoten) enalapril (e.g., available under the brand name Vasotec) fosinopril (e.g., available under the brand name Monopril) lisinopril (e.g., available under the brand name Prinivil) moexipril (e.g., available under the brand name Univasc) quinapril (e.g., available under the brand name AccupriL) ramipril (e.g., available under the brand name Altace) trandolapril (e.g., available under the brand name Mavik), and the like); sympathomimetics (e.g., trimethaphan, clondine, reserpine, guanethidine, and the like); calcium channel blockers (e.g., amlodipine besylate (e.g., available under the brand name Norvasc), diltiazem hydrochloride (e.g., available under the brand names Cardizem CD, Cardizem SR, Dilacor XR, Tiazac), felodipine plendil isradipine (e.g., available under the brand names DynaCirc, DynaCirc CR), nicardipine (e.g., available under the brand name Cardene SR), nifedipine (e.g., available under the brand names Adalat CC, Procardia XL), nisoldipine sulfur (e.g., available under the brand name Sular), verapamil hydrochloride (e.g., available under the brand names Calan SR, Covera HS, Isoptin SR, Verelan) and the like); sodium channel blockers, (e.g., moricizine, propafenone, encainide, flecainide, tocainide, mexiletine, phenyloin, lidocaine, disopyramide, quinidine, procainamide, and the like); vasopressin inhibitors (e.g., atosiban (Tractocile), AVP V1a (OPC-21268, SR49059 (Relcovaptan)), V2 (OPC-31260, OPC-41061 (Tolvaptan), VPA-985 (Lixivaptan), SR121463, VP-343, FR-161282) and mixed V1a/V2 (YM-087 (Conivaptan), JTV-605, CL-385004) receptor antagonists, and the like); peripheral adrenergic inhibitors (e.g., guanadrel (e.g., available under the brand name Hylorel), guanethidine monosulfate (e.g., available under the brand name Ismelin), reserpine (e.g., available under the brand names Serpasil, Mecamylamine, Hexemethonium), and the like); blood vessel dilators (e.g., hydralazine hydrocholoride (e.g., available under the brand name Apresoline), minoxidil (e.g., e.g., available under the brand name Loniten), and the like); central agonists (e.g., alpha methyldopa (e.g., available under the brand name Aldomet), clonidine hydrochloride (e.g., available under the brand name Catapres), guanabenz acetate (e.g., available under the brand name Wytensin), guanfacine hydrochloride (e.g., available under the brand name Tenex), and the like; combined alpha and beta-blockers (e.g., carvedilol (e.g., available under the brand name Coreg), labetolol hydrochloride (e.g., available under the brand names Normodyne, Trandate), and the like); alpha blockers (e.g., doxazosin mesylate (e.g., available under the brand name Cardura), prazosin hydrochloride (e.g., available under the brand name Minipress), terazosin hydrochloride (e.g., available under the brand name Hytrin), and the like); renin inhibitors (e.g., Aliskiren, and the like); oxytocin inhibitors (e.g., terbutaline, ritodrine, and the like), and botulism toxin (or botox) and the like.

Other pharmacological agents may also be employed to treat any one of an inflammatory condition, blood-clotting condition and autonomic nervous system dysfunction such as adrenergia or abnormally high parasympathetic activity/sympathetic activity ratio. For example, the one or more of the following may be employed: adiponectins; phenserines; phosphodiesterase 4 inhibitors; valproate; glucagon and glucagon-like peptide-1 (GLP-1); glucocorticoid receptor blockers (e.g., mifepristone, and the like); nicotine; potassium channel blockers and magnesium channel blockers, e.g., valproate (sodium valproate, valproic acid), lithium; combination diuretics (e.g., amiloride hydrochloride+hydrochlorothiazide (e.g., available under the brand name Moduretic), spironolactone+hydrochlorothiazide (e.g., Aldactazide), triamterene+hydrochlorothiazide (e.g., available under the brand names Dyazide, Maxzide) and the like); potassium sparing diuretics (e.g., amiloride hydrochloride (e.g., available under the brand name Midamar), spironolactone (e.g., available under the brand name Aldactone), triamterene (e.g., available under the brand name Dyrenium), and the like); nitrate compounds (e.g., L-arginine, (e.g., available under the brand names Nitroglycerin Deponit, Minitran, Nitropar, Nitrocine, Nitro-Derm, Nitro Disc, Nitro-Dur, Nitrogard, Nitroglycerin, Nitroglycerin T/R, Nitro-Time, Nitrol Ointment, Nitrolingual Spray, Nitrong, Nitro-Bid, Nitropress, Nitroprex, Nitro S.A., Nitrospan, Nitrostat, Nitro-Trans System, Nitro-Transdermal, Nitro-Time, Transderm-Nitro, Tridil. Pentaerythritol Tetranitrate Peritrate, Peritrate S.A. Erythrityl Tetranitrate Cardilate Isosorbide Dinitrate/Phenobarbital Isordil w/PB Isosorbide Mononitrate Imdur, ISMO, Isosorbide Mononitrate, Monoket Isosorbide Nitrate Dilatrate-SR, Iso-bid, Isordil, Isordil Tembids, Isordil Dinitrate, Isordil Dinitrate LA, Sorbitrate, Sorbitrate SA), and the like); gonadotropin-releasing hormone analogues (GnRH-As); vesicular monoamine transport (VMAT) inhibitors (e.g., reserpine, tetrabenazine, and the like); statins (e.g., atorvastatin (Lipitor R) cerivastatin (Baycol R) fluvastatin (Lescol R) lovastatin (Mevacor R) pravastatin (Pravachol R) simvastatin (Zocor R), and the like); cyclic nucleotide monophosphodiesterase (PDE) inhibitor (e.g., Levitra (vardenafil), Viagra (sildenafil) Cialis (tadalafil)); alcohol (e.g., ethanol); relaxin; estrogen and estrogen analogues and estrogen metabolites; melatonin (including melatonin analogues as noted above) (e.g., 6-chloromelatonin, 2,3-dihydromelatonin, 6-chloro-2,3-dihydromelatonin, N-acetyl-N-2-formyl-5-methoxy kynurenamine, N-acetyl-5-methoxy kynurenamine, and the like); triglyceride lowering agents (e.g., fenofibrate (Tricor) gemfibrozil (Lopid)); niacin; anti-diabetic agents (e.g., acarbose (Precose R) glimepiride (Amaryl R) glyburide Micronase R, Diabeta R) metformin (Glucophage R) Miglitol (Glycet R) pioglitazone (Actos R) repaglinide (Prandin R) rosiglitazone (Avandia R)); cholinergics (e.g., Bethanechol, Oxotremorine, Methacholine, Cevimeline, Carbachol, Galantamine, Arecoline, Levaminsole); acetylcholinesteriase inhibitors (e.g., Edrophonium, Neostigmine, Donepezil, Tacrine, Echothiophate, Diisopropylfluorophosphate, Demecarium, Pralidoxime, Galanthamine, Tetraethyl pyrophosphate, Parathoin, Malathion, Isofluorophate, Metrifonate, Physostigmine, Rivastigmine, Abenonium acetylchol, Carbaryl acetylchol, Propoxur acetylchol, Aldicarb acetylchol); muscarinics (e.g., Muscarine, Pilocarpine); magnesium, magnesium sulfate, and other magnesium salts; dipeptidyl peptidase IV inhibitors (e.g., LAF237 (novartis), P93/01 and P32/98 (Probiodrug AB), valine pyrrolidide (Novo Nordisk)); dhea (e.g., adiponectin, phenserine, phosphodiesterase 4 inhibitor, valproate, and the like); fungi antagonists; Leptin; Galanin like peptide; gonadotropin-releasing hormone inhibitors (e.g., Leuprolide Acetate); testosterone inhibitors (e.g., sprinolactone, cyproterone acetate, and the like); and progesterone inhibitors (e.g., RU486).

Accordingly, in practicing embodiments of the subject methods, an effective amount of an anti-inflammatory, anti-blood clotting or anti-adrenergic agent is administered to a subject to treat the subject for at least one of an inflammatory condition, a blood clotting condition, and a adrenergic condition, and in many embodiment all three of these conditions simultaneously with the administration of just one of an anti-inflammatory agent, anti-blood clotting agent or an anti-adrenergic agent. As noted above, the particular dosage, mode of administration, treatment times, etc., will vary according to a variety of factors, but will generally fall within the ranges conventionally administered for the particular pharmacological agent employed.

The dose of an anti-inflammatory, anti-blood clotting or anti-adrenergic agent administered to a subject, particularly a human, in the context of the present invention should be sufficient to effect a therapeutic reduction in inflammation and/or blood clotting and/or adrenergia, and in many embodiments two or three such conditions, in the subject over a reasonable time frame. The dose will be determined by, among other considerations, the potency of the particular pharmacological agent employed and the condition of the subject, as well as the body weight of the subject to be treated. The size of the dose also will be determined by the existence, nature, and extent of any adverse side-effects that might accompany the administration of a particular compound.

In determining the effective amount of an anti-inflammatory, anti-blood clotting or anti-adrenergic agent in the treatment of inflammation and/or blood clotting and/or adrenergia, the route of administration, the kinetics of the release system (e.g., pill, gel or other matrix), and the potency of the pharmacological agent are considered so as to achieve the desired therapeutic effect with minimal adverse side effects. The particular anti-inflammatory, anti-thrombotic or anti-adrenergic agent employed may be administered to the subject being treated for a time period ranging from a day to a few weeks, consistent with the clinical condition of the treated subject however administration for periods of time longer than a few weeks, e.g., a few months, a year or more, even as long as the lifetime of a subject as noted above, are also contemplated.

As noted above, the dose of pharmacological agent will be different for different subject, condition(s) treated, etc. The following descriptions of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent.

Accordingly, in practicing embodiments of the subject methods, an effective amount of a pharmacological agent (or a plurality of pharmacological agents which may be the same or different type) may be administered to a subject to treat a condition affecting the subject such as sleep apnea. As noted above, the particular dosage, mode of administration, treatment times, etc., will vary according to a variety of factors, but may fall within the ranges conventionally administered for the particular pharmacological agent employed. As noted above, the dose of pharmacological agent will be different for different subject, condition(s) treated, etc. Exemplary treatment protocols are now provided.

Beta-Blocker

As noted above, embodiments may include administering an effective amount of a beta-blocker. Such embodiments may include administering adult oral dosage forms (capsules and tablets) of acebutolol ranging from about 200 milligrams (mgs.) to about 1200 mgs., e.g., from about 200 mgs. to about 800 mgs. Such oral dosages may be administered as a single dose one time a day, two times a day, or divided into two daily doses for an adult, etc.

Embodiments may include administering atenolol. Such embodiments may include administering adult oral dosage forms (e.g., tablets) of atenolol (e.g., available under the brand name TENORMIN) that range from about 25 mgs. to about 100 mgs. once a day. For example, administration may include about 50 mgs. once a day, or about 100 mgs. of atenolol once a day, or about 50 mgs. atenolol two times a day, e.g., for about six to about nine days. Embodiments that include administering atenolol in adult injection dosage forms may include about 5 mgs. given over 5 minutes, repeated ten minutes later. Atenolol may also be administered intravenously in certain embodiments.

Embodiments may include administering adult oral dosage forms (e.g., tablets) of betaxolol to treat a condition. Such embodiments may include administering about 10 mgs. of betaxolol as an adult dosage form once a day.

Embodiments may include administering adult oral dosage forms (e.g., tablets) of bisoprolol (e.g., available under the brand name ZEBETA). Such embodiments may include administering about 5 mgs. to about 10 mgs. of bisoprolol as an adult oral dosage forms (e.g., tablets) once a day.

Embodiments may include administering adult oral dosage forms (e.g., tablets) of carteolol. Adult oral dosage forms (e.g., tablets) of carteolol may include about 0.5 mgs. to about 10 mgs. administered once a day.

Embodiments may include administering esmolol. Esmolol may be administered via iv as follows: loading dose of about 20-30 mg ivp over 1 minute using a 10 mg/ml 10 ml vial and maintenance dose of about 2 To 12 mg/min as titrated to patient response and maintenance infusions may be increased by about 2 to 3 mg/min at 10 minute intervals until the desired response is achieved.

Embodiments may include administering adult oral dosage forms (e.g., tablets) of labetalol. Adult oral dosage forms (e.g., tablets) of labetalol may include about 100 mgs. to about 400 mgs. two times a day. Adult injection dosage forms may include about 20 mgs., e.g., injected slowly over about two minutes with additional injections of about 40 mgs. and about 80 mgs. given about every ten minutes if needed, up to a total of about 300 mgs., instead as an infusion at a rate of about 2 mgs. per minute to a total dose of about 50 mgs. to about 300 mgs.

Embodiments may include administering adult oral dosage forms (e.g., tablets) of metaprolol. Adult oral dosage forms (e.g., tablets) of metoprolol may include about 100 mgs. to 450 mgs. a day, taken as a single dose or in divided doses. For example, embodiments may include administering about 50 mgs. about every six hours for about 24 hours or more and then about 100 mgs. two times a day for about 1 to about 3 months or more, e.g., from about 1 to about 3 years or more. Embodiments may include administering long-acting adult oral dosage forms (extended-release tablets) that may include up to about 400 mgs. once a day. Adult injection dosage forms may include about 5 mgs. every two minutes for about three doses.

Embodiments may include administering adult oral dosage forms (e.g., tablets) of nadolol. Embodiments ay include administering adult oral dosage forms (e.g., tablets) of nadolol that may include about 40 mgs. to about 320 mgs. once a day.

Embodiments may include administering adult oral dosage forms (e.g., tablets) of oxprenolol. Embodiments may include administering adult oral dosage forms (e.g., tablets) of oxprenolol (short-acting) that may include about 20 mgs. three times a day. Embodiments may include administering adult long-acting oral dosage forms (extended-release tablets) that may include about 120 mgs. to about 320 mgs. once a day.

Embodiments may include administering adult oral dosage forms (e.g., tablets) of pentbutolol. Embodiments may include administering adult oral dosage forms (e.g., tablets) of penbutolol that may include about 20 mgs. once a day.

Embodiments may include administering adult oral dosage forms (e.g., tablets) of pindolol. Embodiments may include administering adult oral dosage forms (e.g., tablets) of pindolol that may include about 5 mgs. two times a day-up to about 60 mgs. a day.

Embodiments may include administering adult oral dosage forms (e.g., tablets) of propranolol. Embodiments may include administering adult oral dosage forms (e.g., tablets) of propranolol that may include, for regular (short-acting) oral dosage forms (tablets and oral solution), about 80 mgs. to about 320 mgs. a day taken in two, three, or four divided doses up to about 640 mgs./day in certain embodiments. Embodiments may also include about 10 mgs. to about 40 mgs. three or four times a day for an adult and about 500 micrograms (0.5 mgs.) to about 4 mgs. per kilogram of body weight a day taken in divided doses for children. Embodiments may include administering long-acting adult oral dosage forms (extended-release capsules) that may include about 80 mgs. to about 320 mgs. once a day up to about 640 mgs. once a day. Embodiments may include administering adult injection dosage forms that range from about 1 mg. to about 3 mgs. given at a rate not greater than about 1 mg per minute. The dose may be repeated after about two minutes and again after about four hours if needed. Children may be administered about 10 mgs. to about 100 micrograms (0.01 to 0.1 mg) per kilogram of body weight given intravenously about every six to eight hours.

Embodiments may include administering adult oral dosage forms (e.g., tablets) of sotalol. Embodiments may include administering adult oral dosage forms (e.g., tablets) of sotalol that may include about 80 mgs. two times a day up to about 320 mgs. per day taken in two or three divided doses.

Embodiments may include administering adult oral dosage forms (e.g., tablets) of timolol. Embodiments may include administering adult oral dosage forms (e.g., tablets) of timolol that may include about 10 mgs. two times a day up to about 60 mgs. per day taken as a single dose or in divided doses. For example, up to 30 mgs. once a day or in divided doses.

Aldosterone Antagonists

Embodiments may include administering an aldosterone antagonist. For example, embodiments may include administering adult oral dosage forms (e.g., tablets) of spironolactone that may range from about 50 mgs. to about 400 mgs. daily. Embodiments may include administering adult oral dosage forms (e.g., tablets) of eplerenone that may range from about 50 mgs. to about 100 mgs. daily.

Angiotensin II Receptor Blockades

Embodiments may include administering an angiotensin II receptor blockade. Such embodiments may include administering an adult oral dosage form of candesartan (e.g., ATACAND) to a subject to treat a condition. Exemplary treatment protocols may include administering about 2 mgs. to about 32 mgs. of candesarten daily (i.e., for a 24 hour interval), e.g., about 16 mgs. daily. Embodiments may include administering adult oral dosage forms of irbersarten (e.g., AVAPRO) to a subject to treat a condition. Exemplary treatment protocols may include administering about 75 mgs. to about 100 mgs. or more, e.g., up to about 300 mgs., of irbersarten daily. Embodiments may include administering adult oral dosage forms of losartan (e.g., COZAAR) to a subject to treat a condition. Exemplary treatment protocols may include administering about 25 mgs. to about 50 mgs. or more, e.g., 100 milligrams, of losarten orally once daily or twice daily. Embodiments may include administering adult oral dosage forms of telmisartin (e.g., MICARDIS) to a subject to treat a condition. Exemplary treatment protocols may include administering about 20 mgs. to about 80 mgs. of telmisartin daily. Embodiments may include administering adult oral dosage forms of valsartan (e.g., DIOVAN) to a subject to treat a condition. Exemplary treatment protocols may include administering about 20 mgs. to about 80 mgs. of valsarten once daily. Embodiments may include administering adult oral dosage forms of eprosarten (e.g., TEVETAN) to a subject to treat a condition. Exemplary treatment protocols may include administering about 400 mgs. to about 800 mgs. of eprosarten once daily or twice daily.

Angiotensin Converting Enzyme Inhibitors (ACE Inhibitors)

Embodiments may include administering an ACE inhibitor. Such may include administering adult oral dosage forms of captropil (e.g., CAPOTEN) to a subject to treat a condition. Exemplary treatment protocols may include administering about 12.5 mgs. to about 50 mgs. of captropil over about 8 to about 12 hours. Embodiments may include administering adult oral dosage forms of enalapril (e.g., VASOTEC) to a subject to treat a condition. Exemplary treatment protocols may include administering about 5 mgs. to about 20 mgs. of enalapril once daily. Embodiments may include administering adult oral dosage forms of fosinopril (e.g., MONOPRIL) to a subject to treat a condition. Exemplary treatment protocols may include administering about 10 mgs. to about 80 mgs., e.g., about 20 mgs. to about 40 mgs., of fosinopril daily. Embodiments may include administering adult oral dosage forms of lisinopril (e.g., PRINIVIL) to a subject to treat a condition. Exemplary treatment protocols may include administering about 10 mgs. to about 80 mgs., e.g., about 20 mgs. to about 40 mgs., of lisinopril daily. Embodiments may include administering adult oral dosage forms of moexipril (e.g., UNIVASC) to a subject to treat a condition. Exemplary treatment protocols may include administering about 3.75 mgs. to about 15 mgs., e.g., 7.5 mgs. of moexipril daily. Embodiments may include administering adult oral dosage forms of quinaapril (e.g., ACCUPRIL) to a subject to treat a condition. Exemplary treatment protocols may include administering about 10 mgs. to about 80 mgs, e.g., about 20 mgs., of quinapril once daily. Embodiments may include administering adult oral dosage forms of ramipril (e.g., ALTACE) to a subject to treat a condition. Exemplary treatment protocols may include administering about 2.5 mgs. to about 20 mgs. of ramipril daily. Embodiments may include administering adult oral dosage forms of trandolapril (e.g., MAVIK) to a subject to treat a condition. Exemplary treatment protocols may include administering about 1 mg. to about 4 mgs., e.g., about 2 mgs., of trandolapril daily.

Sympathomimetics

Embodiments may include administering a sympathomimetic. For example, embodiments may include administering trimethaphan via an I.V., e.g., about 0.1 mgs. to about 1.0 mgs./minute, up to about 15 mgs. per minute. Embodiments may include administering by mouth clondine at about 0.1 mgs. to about 2.4 mgs. daily. Embodiments may include administering by mouth reserpine at about 10 mgs. to about 20 mgs. daily. Embodiments may include administering by mouth guanethidine at about 10 mgs. to about 50 mgs. daily.

Calcium Channel Blockers:

Embodiments may include administering a calcium channel blocker. Embodiments may include orally administering amlodipine besylate (e.g., available under the brand name NORVASC), e.g., about 5 mgs. to about 20 mgs. daily; diltiazem hydrochloride (e.g., available under the brand names CARDIZEM CD, CARDIZEM SR, DILACOR XR, TIAZAC) at about 30 mgs. to about 360 mgs. four times per day (for example 180 mgs. to about 360 mgs. divided into four times per day); felodipine plendil at about 2.5 mgs. to about 10 mgs. daily; isradipine (e.g., available under the brand names DYNACIRC, DYNACIRC CR) at about 2.5 mgs. daily; nicardipine (e.g., available under the brand name CARDENE SR) at about 20 mgs. to about 40 mgs. three times per day; nifedipine (e.g., available under the brand names ADALAT CC, PROCARDIA XL) at about 10 mgs. three times per day; nisoldipine (e.g., available under the brand name SULAR) at about 10 mgs. to about 20 mgs. daily; and verapamil hydrochloride (e.g., available under the brand names CALAN SR, COVERA HS, ISOPTIN SR, VERELAN) at about 40 mgs. three times per day.

Sodium Channel Blockers

Embodiments may include administering a sodium channel blocker. For example, embodiments may include administering about 150 mgs. of propafenone by mouth every 8 hours (450 mgs./day) up to about 300 mgs. every 8 hours (90 mgs./day). Embodiments may also include administering about 50 mgs. to about 100 mgs. of flecainide by mouth about every 12 hours up to about 400 mgs./day. Embodiments may include administering about 400 mgs. to about 2400 mgs. of tocainide by mouth about every 8 hours. Embodiments may also include administering about 100 mgs. to about 200 mgs. of phenyloin by mouth three times per day. Embodiments may also include administering about 10-30 mgs of about 1% to about 2% lidocaine IM (the maximum individual dosage typically should not exceed about 4.5 mg/kg of body weight and generally the maximum total dose should not exceed about 300 mgs.). Embodiments may also include administering about 150 mgs. to about 300 mgs. of dispoyramide by mouth about every 6 hours to about every 12 hours, up to about 1600 mgs. per day. Embodiments may also include administering quinidine (e.g., available under the brand name QUINAGLUTE) at about two tablets (648 mgs.; 403 mgs. of quinidine base) of QUINAGLUTE by mouth about every 0.8 hours.

Glucocorticoid Receptor Blockers

Embodiments may include administering a glucocorticoid receptor blocker. For example, embodiments may include administering mifepristone my mouth at about 400 micrograms to about 600 mgs.

Peripheral Andrenergic Inhibitors

Embodiments may include administering a peripheral andrenergic inhibitor. For example, embodiments may include administering about 5 mgs. to about 75 mgs. of guanadrel (e.g., available under the brand name HYLOREL) by mouth e.g., about 5 mgs. two times per day, about 20 to about 75 mgs. per day in divided doses. Embodiments may also include administering about 10 mgs. to about 50 mgs. or more per day of guanethidine monosulfate (e.g., available under the brand name ISMELIN) by mouth. Embodiments may also include administering about 0.05 to about 1.5 mgs. once per day by mouth of reserpine (e.g., available under the brand names SERPASIL, MECAMYLAMINE, HEXEMETHONIUM). Embodiments may also include administering about 2.5 mgs. of mecamylamine two times per day by mouth.

Blood Vessel Dilators

Embodiments may include administering a blood vessel dilator. For example, embodiments may include administering about 10 mgs. to about 50 mgs. of hydralazine hydrocholoride (e.g., available under the brand name APRESOLINE) by mouth four times a day. Embodiments may also include administering about 5 mgs. to about 40 mgs. of minoxidil (e.g., e.g., available under the brand name LONITEN) by mouth once per day.

Central Agonists

Embodiments may include administering a central agonist. For example, embodiments may include administering about 250 mgs. of alpha methyldopa (e.g., available under the brand name ALDOMET) by mouth three times per day or about 500 mgs. to about 2 grams per day divided into 2 to 4 doses. Embodiments may also include administering about 0.1 mgs. to about 0.6 mgs. of clonidine hydrochloride (e.g., available under the brand name CATAPRES) by mouth once per day. Embodiments may also include administering about 4 mgs. of guanabenz acetate (e.g., available under the brand name WYTENSIN) by mouth two times per day (up to about 32 mgs. per day). Embodiments may also include administering about 1 mg. to about 3 mgs. of guanfacine hydrochloride (e.g., available under the brand name TENEX) by mouth once per day.

Combined Alpha and Beta-Blockers

Embodiments may include administering a combined alpha and beta-blocker. For example, embodiments may include administering about 100 mgs. two times per day of labetolol hydrochloride (e.g., available under the brand names NORMODYNE, TRANDATE) by mouth up to about 400 mgs. per day. Embodiments may also include administering about 3.125 mgs. two times per day of carvedilol (e.g., available under the brand name COREG) by mouth up to about 50 mgs. per day.

Alpha Blockers

Embodiments may include administering an alpha and beta-blocker. For example, embodiments may include administering about 1 mg once per day by mouth of doxazosin mesylate (e.g., available under the brand name CARDURA) up to about 16 mgs. per day. Embodiments may also include administering about 0.5 mgs. by mouth of prazosin hydrochloride (e.g., available under the brand name MINIPRESS) two or three times per day (and may include about 6 to about 15 mgs. per day divided into 2 or 3 doses. Embodiments may also include administering about 1 mg. of terazosin hydrochloride (e.g., available under the brand name HYTRIN) by mouth once per day, up to about 5 mgs. per day.

Combination Diuretics

Embodiments may include administering a combined diurentic. For example, embodiments may include administering about 1-2 tablets of amiloride hydrochloride+hydrochlorothiazide (e.g., available under the brand name MODURETIC) once per day for tablets containing 5 mgs. of anhydrous amiloride HCl and 50 mgs. of hydrochlorothiazide). Embodiments may also include administering about 25 mgs. to about 50 mgs. once per day by mouth of spironolactone+hydrochlorothiazide (e.g., available under the brand name ALDACTAZIDE). Embodiments may also include administering about 1 to 2 tablets one per day of triamterene+hydrochlorothiazide (e.g., available under the brand names DYAZIDE, MAXZIDE) for tablets containing 25 mgs. hydrochlorothiazide and 37.5 mgs. triaterene.

Potassium Sparing Diuretics

Embodiments may include administering a potassium sparing diuretic. For example, embodiments may include administering about 5 mgs. to about 20 mgs. by mouth once per day of amiloride hydrochloride (e.g., available under the brand name MIDAMAR). Embodiments may also include administering about 25 mgs. to about 200 mgs. once per day by mouth of spironolactone (e.g., available under the brand name ALDACTONE). Embodiments may also include administering about 1 to 2 tablets once per day of triamterene (e.g., available under the brand name DYRENIUM)) for tablets containing 25 mgs. hydrochlorothiazide and 37.5 mgs. triaterene.

Nitrate Compounds

Embodiments may include administering a nitrate or nitrate compound. For example, embodiments may include administering isosorbide dinitrate (e.g., available under the brand name ISODIL) at about 50 to about 40 mgs. orally four times per day or 40 mgs. sustained release orally every 8 to 12 hours. Embodiments may also include administering isosorbide mononitrate (e.g., available under the brand names ISMO, MONOKET) at about 20 mgs. orally two times per day and/or may include administering extended release initially about 30 mgs. to about 60 mgs. orally once per day. Maximum of about 240 mgs./day. Embodiments may also include administering nitroglycerine ointment, e.g., about 0.5 inches q8h and/or about 0.5 to about 2 inches every 4 to 6 hours, maximum 4 inches every 4 to 6 hours (0.5 inches is about 7.5 mgs.). Embodiments may also include administering nitrobid, e.g., orally about 2.5 mgs. to about 9 mgs. 2 to 4 times per day. Embodiments may also include administering a nitroglycerin patch, e.g., one patch each day applied and removed at bedtime.

Vasopressin Inhibitors

Embodiments may include administering a vasopressin. For example, embodiments may include administering about up to about 6.75 mg administered via IV of atosiban, e.g., 300 micrograms/min to about 100 micrograms/min IV.

Oxytocin Inhibitors

Embodiments may include administering an oxytoxin inhibitor. For example, embodiments may include administering about 0.25 to about IM of terbutaline, typically not more than about 0.5 mgs. within a four hour period. Embodiments may also include administering about 50 micrograms per minute IV of ritodrine, maximum dosage of about 300 micrograms per minute.

Renin Inhibitors

Embodiments may include administering a rennin inhibitor. For example, embodiments may include administering Aliskiren by mouth at about 2 mgs to about 10 mgs./day.

Vesicular Monoamine Transport (VMAT) Inhibitors

Embodiments may include administering a VMAT inhibitor. For example, embodiments may include administering tetrabenazine by mouth at about 150 mgs. to about 200 mgs. once per day. Embodiments may also include administering reserpine at about 50 micrograms to about 500 micrograms one time per day.

Anti-Blood-Clotting

Embodiments may include administering an anti-blood clotting agent. For example, embodiments may include administering about 0.25 mg/kg intravenous bolus of abciximab and/or a continuous intravenous infusion of about 0.125 m g/kg/min (to a maximum of about 10 m g/min) for a period of time, e.g., 12 hours. Embodiments may include administering dipridamole (e.g., AGGRENOX or the like) orally, e.g., one capsule twice daily. Embodiments may include administering anagrlide (e.g., AGRILYN or the like) orally, e.g., initially 0.5 mg orally four times daily or 1 mg orally twice daily or lowest effective dose- to a maximum 10 mg/day. Embodiments may include administering clopiogrel (e.g., PLAVIX or the like) at 75 mg orally once daily. Embodiments may include administering dipridamole (e.g., PERSANTINE or the like) at 75 to 100 mg orally four times daily. Embodiments may include administering eptifabatide (e.g., INTEGRILIN or the like) via IV at 0.5 mcg/kg/min to 180 mcg/kg or 135 mcg/kg and/or (e.g., followed by) 0.5 mcg/kg/min×20-24 hours. For example IV bolus of 180 mcg/kg over 1-2 minutes followed by 2 mcg/kg/min (maximum 15 mg/hr) up to 72 hours. Embodiments may include administering ticlopidine (e.g., TICLID or the like) at 250 mg orally twice daily. Embodiments may include administering tirofibam (e.g., AGGRASTAT or the like) at 0.4 mcg/kg/min to 0.1 mcg/kg/min. Embodiments may include administering ardeparin (e.g., NORMIFLO or the like) at 50 units SC every 12 hours. Embodiments may include administering dalteparin (e.g., FRAGMIN or the like) at 2500 units to 5000 units SC once daily or 120 units/kg to about 10,000 SC every 12 hours. Embodiments may include administering enoxaparin (e.g., LOVENOX or the like) at 30-40 mg SC once daily. Embodiments may include administering lepiudin (e.g., REFLUDAN or the like) at 0.4 mg/kg (max weight of 110 kg) over a15-20 seconds followed by does of 0.15 mg/kg/hr (max weight of 110 kg)×2-10 days as needed. Embodiments may include administering alteplase (e.g., ACTIVASE), t-PA or the like) at 15 mg to 35 mg via IV, e.g., 15 mg via IV bolus followed by 30-35 mg via IV over about 60 minutes. Embodiments may include administering reteplase (e.g., RETEVASE or the like) at 10.8 units IV over 2 minutes repeated in 30 minutes. Embodiments may include administering streptokinase at 1.5 million units N over 60 minutes. Embodiments may include administering aminocaproic acid (e.g., AMICAR or the like) at 4 to 5 grams orally or IV over 1 hour, then 1 gram as needed. Embodiments may include administering cilostazol (e.g., PLETAL or the like) at 50 to 100 mg orally twice daily. Embodiments may include administering pentoxifylline (e.g., TRENTAL or the like) at 400 mg orally three times daily with meals.

Prednisone and Steroids:

As described above, embodiments may include administering an effective amount of prednisone or a steroid. Embodiments may include administering dosages of prednisone or a steroid by mouth at about 5 to about 60 mg/day, once per day. For example, prednisone may be in the form of a solution, syrup or tablet and doses may be given once daily or every other day and about 2.5-15 mg may be taken by a subject 2-4 times daily.

In certain embodiments, the inflammatory condition and/or blood clotting condition and/or adrenergic condition may be a result of a condition, including a disease, of the subject. In such embodiments, the subject methods may include identifying the condition causing the inflammatory condition and/or blood clotting condition and/or adrenergic condition. For example, an inflammatory condition and/or blood clotting condition and/or adrenergic condition may be a result of a cardiovascular condition, a stroke, vasculitis, a vascular disease such as arterial disease, aortic disease and the like, a pulmonary embolism, restenosis of a blood vessel, diabetes, hypercholesteremia, and the like. In certain embodiments, an inflammatory condition and/or blood clotting condition and/or adrenergic condition may be a result of trauma to the subject's body. Accordingly, certain embodiments may include identifying the condition causing or which has the potential to cause, including exacerbating, an inflammatory condition and/or blood clotting condition and/or adrenergic condition.

Modulating at Least a Portion of a Subject's Autonomic Nervous System

As noted above, certain embodiments may include treating a subject for at least one of an inflammatory condition, a blood clotting condition and an autonomic nervous system dysfunction condition such as an adrenergic condition, and in many embodiment all three simultaneously, by modulating at least a portion of the subject's autonomic nervous system to increase the parasympathetic activity/sympathetic activity ratio in a manner effective to treat the subject for the condition(s). Such modulation may be accomplished using any suitable method, including pharmacological modulation and electrical energy modulation. As noted above, in certain embodiments modulation of the autonomic nervous system may be accomplished at least in part by modulating receptors, e.g., beta adrenergic receptors, immunomodulatory receptors, and the like. Methods and devices for treating a subject for a condition by modulating at least a portion of the subject's autonomic nervous system have been described in copending, commonly assigned U.S. patent application Ser. No. 10/661,368, the disclosure of which is herein incorporated by reference.

As methods and devices for treating a subject for a condition by modulating at least a portion of the subject's autonomic nervous system have been described in detail the above-noted copending, commonly assigned US patent application, they will not be described in great detail herein. Briefly, in accordance with the subject invention to treat a subject for at least one of, and in many embodiment two or all three of: an inflammatory condition, blood clotting condition and adrenergic condition such as adrenergia, at least a portion of the autonomic nervous system may be modulated using any suitable technique, including, but not limited to, surgical methods (e.g., surgical isolation of an effector structure from sympathetic and/or parasympathetic innervation, i.e., surgically isolating an effector structure from one or more sympathetic and/or parasympathetic nerve fibers associated with it); ablation (permanently or reversibly ablating a nerve by employing energy delivery devices or cryotherapy); cryoablation; thermoablation; microwave energy; focus ultrasound; magnetic fields including internal and external magnetic fields; laser energy; optical energy; radiofrequency energy; pacing mechanisms (e.g., implantable electrode-based pacing systems, external magnetic-based pacing system, and the like); transcutaneous electrical nerve stimulation ("TENS") or transmagentic stimulation ("TMS") (see for example George, M. Stimulating the Brain. Sci Amer 2003 September); pharmacological modulation and electrical modulation. Certain embodiments may include employing an electric energy supplying device to modulate at least a portion of the autonomic nervous system wherein the device may incorporate an immunomodulator such as a steroid or the like on a subject contacting surface. A device may be permanently or temporarily implanted.

Accordingly, embodiments of the subject invention includes modulating at least a portion of a subject's autonomic nervous system to increase the parasympathetic activity/sympathetic activity ratio, i.e., increase parasympathetic activity relative to sympathetic activity to treat a subject for at least one of, and in many embodiment simultaneously two or even all three of: an inflammatory condition and/or blood clotting condition and/or adrenergic condition. Increasing the parasympathetic activity/sympathetic activity ratio may be achieved by stimulating the parasympathetic system to increase activity in at least a portion of the parasympathetic system, e.g., stimulating at least one parasympathetic nerve fiber. Alternatively or in addition to stimulating at least one parasympathetic nerve fiber to increase activity, increasing the parasympathetic activity/sympathetic activity ratio may be achieved by inhibiting activity in the sympathetic system, e.g., inhibiting activity in at least one sympathetic nerve fiber. As noted above, increasing the parasympathetic activity/sympathetic activity ratio may also be accomplished by modulating receptors, e.g., to stimulate or inhibit signal transduction and/or increase or decrease binding affinity.

While the subject methods are described primarily with respect to embodiments that result in increasing the parasympathetic activity/sympathetic activity ratio, it is to be understood that the subject invention is not limited to embodiments wherein the parasympathetic activity/sympathetic activity ratio is increased and as such it is to be understood that the subject invention includes embodiments for modulating at least a portion of a subject's autonomic nervous system to decrease the parasympathetic activity/sympathetic activity ratio, i.e., decrease parasympathetic activity relative to sympathetic activity, and the like.

In embodiments that include modulating at least a portion of a subject's autonomic nervous system to treat the subject for a condition such as an inflammatory condition and/or thrombotic condition and/or adrenergic condition, a sympathetic bias may be the normal or desired state, but the ratio of the two systems may be abnormal or otherwise contributing to a condition (e.g., inflammation, blood clotting, adrenergia, and the like) such that the ratio is adjusted but still provides a sympathetic bias (or may be adjusted to provide a parasympathetic bias). Increasing parasympathetic activity may also be desired in instances where, prior to the application of autonomic nervous system-modulating electrical energy and/or the administration of an effective amount of at least one pharmacological agent, parasympathetic activity is higher than the sympathetic activity, but the differential between the two systems needs to be modulated such as increased further, e.g., the sympathetic activity is normal or above normal (i.e., abnormally high) and/or the parasympathetic activity is normal or below normal (i.e., abnormally low) or above normal (i.e., abnormally low). For example, such instances may occur where a subject has normal or above normal parasympathetic function, but also has elevated sympathetic function. Other instances may include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low. The above-described examples of instances where increasing parasympathetic activity may be desired is exemplary only and is in no way intended to limit the scope of the invention and other instances where increasing parasympathetic activity may be desired will be apparent to those of skill in the art.

While the subject methods are described primarily with respect to increasing activity in the parasympathetic system, it is to be understood that this is for exemplary purposes only and is in no way intended to limit the scope of the invention as activity may also, or in addition, be increased in at least a portion of the sympathetic nervous system.

To accomplish the modulation of at least a portion of a subject's autonomic nervous system electrical energy (electrical modulation) may be applied to at least a portion of a subject's autonomic nervous system, where such electrical energy may be excitatory or inhibitory and in certain embodiments may include both excitatory and inhibitory stimulation. Embodiments of the subject methods may also, in addition to or instead of electrical energy, include administering at least one pharmacological agent (pharmacological modulation) to said subject to modulate at least a portion of a subject's autonomic nervous system, where the pharmacological agent may be employed to increase activity in at least a portion of the autonomic nervous system and/or decrease activity in at least a portion of the autonomic nervous system. Pharmacological agents of interest include, but are not limited to, agents described herein.

Embodiments of the subject invention may include electrically modulating (i.e., applying electrical energy to) at least a portion of a subject's autonomic nervous system and/or pharmacologically modulate at least a portion of the autonomic nervous system to achieve a desired parasympathetic activity/sympathetic activity ratio, i.e., a desired level of parasympathetic activity relative to sympathetic activity. As described above, in certain embodiments the desired ratio is analogous to a parasympathetic activity/sympathetic activity ratio observed in a healthy (e.g., a subject not experiencing the condition for which the subject is being treated such as not experiencing inflammation and/or thrombosis and/or adrenergia), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the practice of the subject methods to treat the subject for thrombosis and/or inflammation and/or adrenergia may be analogous to the parasympathetic activity/sympathetic activity ratio observed in a healthy human ranging in age from about 20 years old to about 25 years old.

As noted above, embodiments of the subject invention may include treating a subject for a condition such as an inflammatory condition and/or thrombotic condition and/or adrenergic condition by pharmacologically modulating at least a portion of the subject's autonomic nervous system, e.g., to increase the parasympathetic activity/sympathetic activity ratio or increase parasympathetic activity relative to sympathetic activity. By "pharmacologically modulating at least a portion of a subject's autonomic nervous system" is meant altering or changing at least a portion of an autonomic nervous system by pharmacological means to provide a change, alteration or shift in at least one component or aspect of the autonomic nervous system, as will be described in greater detail below. The modulation of the autonomic nervous system may affect central motor output and/or nerve conduction and/or transmitter release and/or synaptic transmission and/or receptor activation, and in many embodiments is a change that provides an increase in the parasympathetic activity/sympathetic activity ratio (as used herein, "activity" and "function' are used interchangeably). For example, at least a portion of the autonomic nervous system may be pharmacologically modulated to alter, shift or change parasympathetic activity and/or sympathetic activity from a first state to a second state, where the second state is characterized by an increase in the parasympathetic activity/sympathetic activity ratio relative to the first state. In certain embodiments, the subject invention provides methods of increasing activity in at least one parasympathetic nerve fiber to achieve an increase in the parasympathetic activity/sympathetic activity ratio. In certain embodiments the subject invention provides methods of inhibiting activity in at least one sympathetic nerve fiber to achieve an increased parasympathetic activity relative to sympathetic activity. Still further, in certain embodiments the subject invention provides methods of both increasing activity in at least one parasympathetic nerve fiber and inhibiting activity in at least one sympathetic nerve fiber to achieve the desired result.

Accordingly, in certain embodiments of the subject methods the parasympathetic activity/sympathetic activity ratio is increased. By "increased ratio of parasympathetic activity to sympathetic activity" and analogous terms is meant that this ratio is increased in at least a portion of the autonomic nervous system, where the increase is at least great enough to treat a given condition. While the ratio of sympathetic function/parasympathetic function may be increased according to embodiments of the subject invention to treat a subject for, e.g., inflammation and/or blood clotting and/or adrenergia, the net result may be a sympathetic bias (i.e., sympathetic dominance), parasympathetic bias (i.e., parasympathetic dominance) or the activities of the sympathetic system and parasympathetic system may be substantially equal (i.e., neither is dominant). By "bias" is meant that the particular "biased" component of the autonomic nervous system has a higher activity level than the other component. For example, a sympathetic bias refers to a higher level of sympathetic activity than parasympathetic activity, and vice versa, where such bias may be systemic or localized. The net result of the subject methods to treat a condition may be higher or greater sympathetic activity relative to parasympathetic activity in at least the area of the autonomic system targeted or rather in need of modulation, higher or greater parasympathetic activity relative to sympathetic activity in at least the area of the autonomic system targeted or rather in need of modulation, or substantially equal activity levels of sympathetic activity and parasympathetic activity. For example, embodiments of the subject methods may include treating a subject for sympathetic bias and/or inflammation and/or blood clotting by administering an effective amount of an anti-adrenergic agent to the subject, where the administered agent may result in a sympathetic bias, parasympathetic bias or substantially equivalent activity levels of parasympathetic activity and sympathetic activity. Accordingly, embodiments include treating a subject for sympathetic bias and an inflammatory condition and a blood clotting condition at the same time by administering an effective amount of a single pharmacological agent, e.g., an anti-adrenergic agent, to the subject.

In practicing the subject methods, at least a portion of a subject's autonomic nervous system is modulated, e.g., electrically and/or pharmacologically. Modulation according to the embodiments of the subject methods may result in an increase in parasympathetic activity relative to sympathetic activity (i.e., increase parasympathetic activity/sympathetic activity ratio). As noted above, the electrical and/or pharmacological modulation may provide an increase in function of at least a portion of the autonomic system, e.g., increase function in at least one parasympathetic nerve fiber, and/or provide a decrease in function or dampening of a portion of the autonomic system, e.g., may inhibit activity in at least one sympathetic nerve fiber or inhibit nerve pulse transmission.

Exemplary pharmacological agents that may be employed to modulate a portion of a subject's autonomic nervous system to treat the subject for inflammatory condition and/or blood clotting condition and/or adrenergic condition include, but are not limited to, those described herein and elsewhere.

As mentioned above, embodiments also include targeting a receptor to modulate it in a manner to increase parasympathetic activity/sympathetic activity ratio in at least a portion of the autonomic nervous system to treat a subject for at least one of an inflammatory condition, a blood clotting condition and an autonomic nervous system dysfunction condition. The activity of a receptor may be increased or decreased (e.g., a receptor may be blocked), depending on the desired result, e.g., whether it is desirable to increase parasympathetic activity/sympathetic activity ratio or decrease the parasympathetic activity/sympathetic activity ratio. For example, the particulars as to receptor modulation may depend on, e.g., whether it is desirable to increase ligand binding affinity to the receptor, decrease ligand binding affinity, increase signal transmission, decrease signal transmission, etc. Receptors that may be targeted include sympathetic receptors and parasympathetic receptors.

For example, pro-sympathetic receptors, the activation of which may promote inflammation (and which may be referred to as sympathetic inflammatory receptors), and which may be targeted to treat a subject for at least one of an adrenergic condition and a blood clotting condition include, but are not limited to the following receptors: catecholamine, noradrenaline, interferon alpha, interferon beta, interferon gamma, CD 20, CD 3, Interleukin 1-13 and 18, estrogen, testosterone, gonadotropin releasing Hormone, oxytocin, alcohol, adrenaline, dehydroepiandrostonedione, glucagons-like peptide 1, leptin, and histamine, etc.

Pro-sympathetic receptors, the activation of which may promote blood-clotting (and which may be referred to as sympathetic or pro-sympathetic blood clotting receptors), and which may be targeted to treat a subject for at least one of an inflammatory condition and an adrenergic condition include, but are not limited to the following receptors: prothrombin, thrombin, fibrinogen, etc.

Pro-sympathetic receptors, the activation of which may promote adrenergia, and which may be targeted to treat a subject for at least one of a blood clotting condition and an adrenergic condition (and which may be referred to as adrenergic receptors), include, but are not limited to the following receptors: beta receptor, alpha receptor, aldosterone, anti-diuretic hormone, angiotensin I, angiotensin II, renal distal tubule transporters, loop of henle transporters, renal proximal tubule transporters, cholinergic, sodium channel, calcium channel, etc.

Pro-parasympathetic receptors, the activation of which may promote inflammation, and which may be targeted to treat a subject for at least one of a blood clotting and an adrenergic condition (and which may be referred to as parasympathetic or pro-parasympathetic inflammatory receptors), include, but are not limited to the following receptors: relaxin, nicotoine, muscarinic, phosphodiesterase, cholinergic, magnesium channel, alchohol, progesterone, etc.

Embodiments also include modulating (e.g., activating or de-activating) one or more enzymes in a manner to increase parasympathetic activity/sympathetic activity ratio or decrease parasympathetic activity/sympathetic activity in at least a portion of the autonomic nervous system to treat a subject for at least one of an inflammatory condition, a blood clotting condition and an autonomic nervous system dysfunction condition.

For example, pro sympathetic enzymes that promote inflammation that may be modulated to treat a subject for at least one of an adrenergic condition and a blood clotting condition include, but are not limited to the following enzymes: HMG CoA reductase, acetylcholinesterase, vesicular monoamine transporter, dipeptidyl peptidase IV etc.

Pro sympathetic enzymes that promote blood-clotting that may be targeted to treat a subject for at least one of an inflammatory condition and an adrenergic condition include, but are not limited to the following enzymes: Factor Va, Factor VII, Factor VIIa, Factor VIIIa, Factor IX, Factor IXa, Factor X, Factor Xa, Factor XI, Factor XIa, Factor XII, Factor XIIa, Factor XIIIa, etc.

Pro sympathetic enzymes that promote adrenergia that may be targeted to treat a subject for at least one of a blood clotting condition and an adrenergic condition include, but are not limited to the following enzymes: angiotensin converting enzyme, rennin, etc.

Pro parasympathetic enzymes that are inflammatory that may be targeted to treat a subject for at least one of a blood clotting and an adrenergic condition include, but are not limited to the following enzymes: nitric oxide, phosphodiesterase, etc.

Feedback Loops

Embodiments of the subject invention may include observing (including measuring) one or more physiological or biologic aspects of a subject and employing the observed one or more aspects as an indicator of the state of the autonomic nervous system modulation according to the subject inventions. Stated otherwise, embodiments include a closed-loop system in which a variable is used as an indicator of state of the autonomic nervous system and may be employed as a trigger to initiate, terminate or adjust modulation of the parasympathetic activity/sympathetic activity ratio in a manner to treat a subject for a condition. In some aspects, a processor for controlling interface functions executes instructions based on measurements obtained by a detector or other measurement componentry. For example, a processor for controlling interface functions may initiate, adjust or terminate a given treatment protocol, including direct movement of a device for administering a treatment protocol according to the subject invention (e.g., an electrical energy delivering device, pharmaceutical agent delivery device (implantable or otherwise), etc., in response to a measurement obtained. In some aspects, aspects of the subject methods respond to feedback from a monitoring system which monitors one or more biological or physiological functions of a subject being treated. A variable may be measured and the parasympathetic activity/sympathetic activity ratio may be modulated in a manner to alter the variable. Once a predetermined target variable measurement is achieved, modulation may be terminated or adjusted to maintain the achieved state.

Embodiments may include, prior to and/or during and/or after modulation of the ANS to treat a subject for an inflammatory condition and/or blood clotting condition and/or adrenergia, determining and/or monitoring-continuously or periodically, any of such conditions, including determining the state of the ANS, e.g., the parasympathetic activity/sympathetic activity ratio. For example, embodiments may include determining whether an inflammatory condition and/or blood clotting condition and/or adrenergia is present. As described above, monitoring of one or more physiological or biologic functions of a subject may be employed in a feedback system whereby modulation of at least a portion of the ANS may be performed according to (i.e., tailored to or based upon) an observed physiological or biologic function.

For example, in the case where pulmonary gas is monitored before and/or during and/or after ANS modulation, the particulars of a pharmacological modulation and/or electrical modulation may be based on the determined pulmonary gas levels such that the amount of pharmacological agent or electrical stimulation may be continually or periodically adjusted until a predetermined, e.g., normal, pulmonary gas level is obtained, at which time ANS modulation may be terminated. For example, the dosage of a given agent may be based on a determined pulmonary gas level. This monitoring and modulation of ANS may be performed automatically, e.g., by way of suitable componentry such that a physiological aspect of a. subject may be repeatedly monitored a given ANS modulation protocol and may be adjusted one or more times based on the results of the monitoring. In many embodiments, an ANS modulation protocol may be continued until a particular level or quality of one or more physiological or biologic aspects are obtained, i.e., a predetermined parameter may be targeted and the ANS may be modulated until that predetermined parameter is achieved. In certain embodiments, a targeted level or quality of a physiological and/or biologic aspect is analogous to the level or quality of a normal subject, as described above. In the below-described exemplary physiological aspects that may be employed in such a feedback loop system, reference values are indicated in parenthesis such that in certain embodiment a reference value may be a target value and once observed, modulation of the ANS may be terminated. Accordingly, in certain embodiments a given ANS modulation protocol may be performed until a time at which a predetermined level or quality of a physiological aspect or biologic aspect of a subject is observed, such as a reference value. Any suitable method may be employed for such observing, determining and monitoring where such methods are known in the art and include methods described herein. In certain embodiments, the determination of pulmonary gases may be employed (reference: alveolar oxygen 600-713 mm Hg).

In certain embodiments, the determination of serum blood gases may be employed (reference: ph range 7.1 to 7.7; arterial $pCO_2$ range 10 mm Hg to 80 mm Hg; arterial $pO_2$ range from 50 mmHg to 110 mmHg; arterial bicarbonate range 10 meq to 40 meq/L; alveolar/oxygen ratio of 1.0 to 0.6; alveolar to arterial gradient of 5 to 120 mHg; venous oxygen saturation 30% to 80%).

In certain embodiments aspects measured during an overnight sleep study may be employed. Sleep study parameters include, but are not limited to the following: sleep state (EEG leads); electrooculogram; EMG; airflow at nose and mouth (via thermistor, capnography, mask and pneumotachygraph, or other methods); chest and abdominal wall motion (impedance or inductance plethysmography or other); electrocardiogram; pulse oximetry including pulse waveform; end tidal carbon dioxide; video camera monitoring with sound montage; transcutaneous oxygen and carbon dioxide tensions; nasal pressure flow measurements; esophageal manometry; continuous noninvasive blood pressure monitoring; autonomic nervous system tone using finger tonometry. Sleep study parameters that may be employed include, but are not limited to: sleep latency (reference: 0-1 hour); total sleep time (reference: 0-12 hours); percent REM sleep (reference 0-40% total sleep time); percent stage 3-4 non-REM sleep (reference 0-50% of total sleep time); respiratory arousal index (reference 0-40/hour total sleep time); periodic leg movements (reference 0-40/hour total sleep time); apnea index (reference 0-20/hour of total sleep time); hypopnea index (reference 0-40/hour of total sleep time); nadir oxygen saturation (reference 40-100%); mean oxygen saturation (reference 40-100%); desaturation index (reference 0-40 defined as >4% for 5 seconds/hour of total sleep time); highest carbon dioxide (reference 10 to 80 mmHg); carbon dioxide>45 mm Hg (reference 0-60% of total sleep time).

In certain embodiments, the determination of cardiopulmonary physiological parameters may be employed that such as, but not limited to: cardiac output (reference: 1 to 6 L/min); cardiac index (reference: 0.5 to 6 L/min/m2); central venous pressure (reference: 3 to 30 cm H20); right arterial pressure (reference: 1-30 mm Hg); right ventricular systolic pressure (reference: 5 to 50 mm Hg); right ventricular diastolic pressure (reference: 1 to 50 mm Hg); pulmonary arterial systolic pressure (reference: 5 to 50 mm Hg); pulmonary arterial diastolic pressure (reference: 1 to 30 mm Hg); mean pulmonary arterial pressure (reference: 5 to 50 mm Hg); pulmonary capillary wedge pressure (reference: 1 to 20 mm Hg).

In certain embodiments, the determination of pulmonary function and spirometry parameters may be employed that such as, but not limited to: tidal volume (reference: 2 mL/kg to 20 ml/kg or 20-80% of predicted); total lung capacity or TLC (reference: 3 to 10 liters or 20-120% of predicted); residual volume (reference: 0.5 to 5 L or 20-120% of predicted); forced expiratory volume in 1 second or FEV1 (reference: 0.5 to 6 liters or 20-120% of predicted); functional vital capacity or FVC (reference: 0.5 to 6 liters or 20-120% of predicted); FEV1/FVC ratio (reference: 20-120%); forced expiratory flow or FEF 25-75 (reference: 50 to 150%); peak expiratory flow rate (reference: 60-120%); forced expiratory time (reference: 0-20 seconds); corrected diffusion capacity or DLCO (reference: 60-140%); corrected QT interval (reference: less than about 600).

In certain embodiments, the determination of serum markers may be employed such as, but not limited to: catecholamine levels; acetylcholine levels (reference 300-2000 IU/L); aldosterone levels (reference 5-150 nmol/day); renin levels (reference 3-200 uU/mL); vasopressin levels (reference 1-20 pg/ml); angiotensin converting enzyme levels (reference 5-200 U/L); interleukin 1-3 and 5-13 and 18; interleukin-4; interferon alpha and beta; interferon gamma; tumor necrosis factor alpha; transforming growth factor; hemoglobin A1C (reference 2.0-12%); fasting glucose (reference fasting 1.0-10.0 mmol/L); high density lipoprotein (10-90); low density lipoprotein (60-200); triglyceride (reference 0.5 to 4.0 mmol/L); beta natriuretic peptide (reference 0-100 pg/mL); alpha natriuretic peptide (reference. 0-50 pg/mL); erthythrocyte sedimentation rate (ESR) (reference 1-200 mm/Hour); C-reactive protein (CRP) (reference 1-80 mg/L); transferring (reference 0.5 to 6 g/L); hemoglobin (reference normal hemoglobin is 25 to 300 gm/L); hematocrit (reference 25-60%); ferritin (reference 5 to 600 µg/L); iron (reference 5 to 100 µmol/L); cholinesterase (reference—200-2500 IU/L); urine adrenaline (reference adrenaline 0-200 nmol/day); unrine noradrenaline (reference 0-1600 nmol/day); urine dopamine (reference 0-7000 nmol/day); adrenocorticotrophic hormone (ACTH) (reference 0 to 40 pmol/L); antidiuretic hormone (reference 1-20 pg/mL); thrombin clotting time (reference—5-30 seconds); serum total cholesterol (reference 100-300); and the like.

Other physiologic or biologic aspects include, but are not limited to: body mass index (reference<40); systolic blood pressure (reference 90-180 mmHg); diastolic blood pressure (30-100 mmHg); pulse pressure (reference 20-40 mmHg); heart rate (reference 30-150 beats/min in adults, 30-200 beats/min in children); corrected QT interval (reference<600); increasing heart rate variability; increasing respiratory sinus arrhythmia; and the like.

In certain embodiments, based the observed measurement of one or more of the above, ANS modulation may be initiated, altered or terminated to treat a subject for a condition. In this manner, continual adjustments may be made to tailor a treatment protocol to a particular physiological or biological state of a subject.

Utility

The subject methods find use in a variety of applications in which it is desired to treat a subject for an inflammatory condition and/or a blood clotting condition and/or an adrenergic condition, and in many embodiments the subject and a blood clotting condition and an adrenergic condition.

The terms "treatment", "treating" and the like are used herein to generally mean obtaining a desired pharmacologic and/or physiologic effect, e.g., reduction of inflammation and/or thrombosis and/or adrenergia. The effect may be prophylactic in terms of completely or partially preventing a condition or symptom thereof and/or may be therapeutic in terms of a partial or complete cure for the condition and/or adverse effect attributable to the condition. "Treatment" as used herein covers any treatment of a condition in a mammal, particularly a human, and includes: (a) preventing a condition from occurring in a subject who may be predisposed to the condition but has not yet been diagnosed as having it; (b) inhibiting the condition, e.g., arresting its development; or (c) relieving the condition. Moreover, suitable subjects of this invention include those who have and those who have not previously been afflicted with inflammation and/or thrombosis and/or adrenergia, those that have previously been determined to be at risk for inflammation and/or thrombosis and/or adrenergia, and those who have been initially diagnosed or identified as being afflicted with or experiencing inflammation and/or blood clotting and/or adrenergia.

A variety of subjects are treatable according to the subject methods. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans.

The methods of the subject invention generally involve administering to a mammal a pharmacological agent such as an anti-inflammatory agent, anti-blood clotting agent or anti-adrenergic agent in an amount effective to reduce inflammation and/or thrombosis and/or adrenergia, where in many embodiment the amount is effective to reduce all three conditions concurrently. An effective amount of an anti-inflammatory, anti-thrombotic or anti-adrenergic agent may reduce inflammation and/or thrombosis and/or adrenergia by at least about 1%, e.g., at least about 5%, e.g., at least about 10%, e.g., at least about 20%, e.g., at least about 25%, e.g., at least about 30%, e.g., at least about 35%, e.g., at least about 40%, e.g., at least about 45%, e.g., at least about 50%, e.g., at least about 55%, e.g., at least about 60%, e.g., at least about 65%, e.g., at least about 70%, e.g., at least about 75%, or more, when compared to an untreated (e.g., a placebo-treated) control.

Whether inflammation and/or blood clotting and/or adrenergia are reduced may be determined using any known method. Methods of determining an effect of an agent on inflammation and/or thrombosis and/or adrenergia are known in the art.

The subject methods find use in the treatment of a variety of different conditions, including inflammation and/or blood clotting and/or adrenergia conditions. In many embodiments, the subject methods are methods of treating a subject for two or more of, including all three of inflammation and/or blood clotting and/or adrenergia, simultaneously by the administration of an effective amount of one of and anti-inflammatory agent, an anti-blood clotting agent and an anti-adrenergic agent. In certain embodiments, the inflammation and/or blood clotting and/or adrenergia may be a result of a condition, including a disease, of the subject. In such embodiments, the subject methods may include identifying a condition causing the inflammation and/or blood clotting and/or adrenergia, where in certain embodiments an underlying condition may be treated as well.

In certain embodiments, the subject methods are methods of treating inflammation and/or blood clotting and/or adrenergia that are a result of a cardiovascular condition. For example, cardiovascular conditions that may result in inflammation and/or blood clotting and/or adrenergia include, but are not limited to, atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, arrhythmia, fatal arrythmias, coronary syndromes, coronary vasospasm, sick sinus syndrome, bradycardia, tachycardia, thromboembolic disease, deep vein thrombosis, coagulopathy, disseminated intravascular coagulation ("DIC"), mesenteric ischemia, syncope, venous thrombosis, arterial thrombosis, malignant hypertension, secondary hypertension, primary pulmonary hypertension, secondary pulmonary hypertension, raynaud's, and paroxysmal supraventricular tachycardia.

In such embodiments wherein a subject is treated for inflammation and/or blood clotting and/or adrenergia that has resulted from a cardiovascular condition, the subject methods may include identifying the cardiovascular condition. Methods for identifying a cardiovascular condition such as any one of the cardiovascular conditions described above, are known in the art.

In certain embodiments, the subject methods are methods of treating inflammation and/or blood clotting and/or adrenergia that are a result of a stroke experienced by the subject. In such embodiments wherein a subject is treated for inflammation and/or blood clotting and/or adrenergia that has resulted from a stroke, the subject methods may include identifying that the subject has experienced a stroke. Methods for identifying whether a stroke has occurred in a subject are known in the art and include, but are not limited to, imaging techniques such as computed tomography (CT), magnetic resonance imaging (MRI), ultrasound such as carotid ultrasound (also called Doppler or duplex sonography), transcranial duplex sonography, and the like, cerebral angiography, positron-emission tomography (PET), single photon-emission computed tomography (SPECT); heart evaluations, e.g., using an electrocardiogram (ECG) or echocardiogram (e.g., transthoracic echocardiogram (TTE) and transesophageal echocardiogram (TEE)); blood tests, e.g., to determine clotting times, to check electrolytes (potassium, calcium, sodium), and to measure factors indicating liver or kidney problems, measurement of blood sugar levels, measurements of the amino acid glutamate; examination of spinal fluid; identification of a bruit; measuring blood pressure; performing a Face, Arm, Speech Test (FAST); and the like.

In certain embodiments, the subject methods are methods of treating inflammation and/or blood clotting and/or adrenergia that are a result of vascultis. In such embodiments wherein a subject is treated for inflammation and/or blood clotting and/or adrenergia that have resulted from vasculitis, the subject methods may include identifying the vasculitis. Methods for identifying vasculitis are known in the art.

In certain embodiments, the subject methods are methods of treating inflammation and/or blood clotting and/or adrenergia that are a result of arterial disease. In such embodiments wherein a subject is treated for inflammation and/or blood clotting and/or adrenergia that have resulted from arterial disease, the subject methods may include identifying the arterial disease. Methods for identifying arterial disease are known in the art.

In certain embodiments, the subject methods are methods of treating inflammation and/or blood clotting and/or adrenergia that are a result of a pulmonary embolism. In such embodiments wherein a subject is treated for inflammation and/or blood clotting and/or adrenergia that have resulted from a pulmonary embolism, the subject methods may include identifying the pulmonary embolism. Methods for identifying a pulmonary embolism are known in the art.

In certain embodiments, the subject methods are methods of treating inflammation and/or blood clotting and/or adrenergia that are a result of restenosis of a blood vessel. In such embodiments wherein a subject is treated for inflammation and/or blood clotting and/or adrenergia that have resulted from restenosis of a blood vessel, the subject methods may include identifying the restenosis. Methods for identifying restenosis are known in the art.

In certain embodiments, the subject methods are methods of treating inflammation and/or blood clotting and/or adrenergia that are a result of diabetes. In such embodiments wherein a subject is treated for inflammation and/or thrombosis and/or adrenergia that have resulted from diabetes, the subject methods may include identifying the diabetes. Methods for identifying diabetes are known in the art.

In certain embodiments, the subject methods are methods of treating inflammation and/or blood clotting and/or adrenergia that are a result of hypercholesteremia. In such embodiments wherein a subject is treated for inflammation and/or thrombosis and/or adrenergia that have resulted from hypercholesteremia, the subject methods may include identifying the hypercholesteremia. Methods for identifying hypercholesteremia are known in the art.

Kits

Also provided are kits for practicing the subject methods. The subject kits may vary greatly in regards to the components included depending on the particular condition(s) treated, etc. For example, kits may include one or more pharmacological agents in suitable form(s) such as anti-inflammation agents, anti-blood clotting agents, and anti-adrenergia agents. A given pharmacological agent may be present in a kit in varying dosages. A kit may also include more than type of pharmacological agent. The dosage amount of the one or more pharmacological agents provided in a kit may be sufficient for a single application or for multiple applications.

In certain embodiments, multiple dosage amounts of a pharmacological agent may be present in a kit. In those embodiments having multiple dosage amounts, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit may be dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intravaginal, endocervical, intrathecal, intranasal, intravesicular, on the eye, in the ear canal, intraperiactivityal, intradermal, transdermal, intracheal, etc. Accordingly, certain systems may include a suppository applicator, syringe, I.V. bag and tubing, electrode, inhaler, transdermal patch or film, etc.

Kits may also include an electrical energy supplying device, as described above. Accordingly, subject kits may include an energy supplying device such that they may include at least one electrode for electrically modifying at least a portion of a subject's autonomic nervous system in accordance with the subject invention, as described above. In certain embodiments, the energy supplying device provided in a kit is an implantable device, or at least certain components such as one or more electrodes, may be implantable. Certain kits may include a plurality of electrodes, where some or all may be the same or some or all may be different. For example, certain kits may include at least a first electrode for electrically modulating activity at least a portion of the sympathetic system and at least a second electrode for electrically modulating activity in at least a portion of the parasympathetic system. In certain embodiments, a subject kit may include a "test" electrode, as described above such as a radiofrequency stimulating electrode. Still further, one or more electrodes may be included in a kit which, instead of or in addition to delivering electric impulses to at least a portion of the autonomic nervous system, delivers an autonomic nervous system pharmacological agent to at least a portion of the autonomic nervous system. Kits according to the subject invention typically also include an energy source such as a battery or generator, where in certain embodiments the energy source may be implantable, and may also include one or more leads or wires for coupling the one or more electrodes to an energy source.

Devices for delivering, e.g., implanting, an electrical energy supplying device and/or a drug delivery device to a target site of a subject such as into the body cavity of a subject may also be included in the subject kits. For example, an endoscope, introducer needle, and the like may be provided.

The subject kits may also include instructions for how to practice the subject methods. For example, instructions may include how to administer the one or more pharmaceutical agents provided in the kit to treat a subject for inflammation and/or thrombosis and/or adrenergia. Instructions may include how to use an energy supplying device provided in the kit in the practice of the subject methods may also be provided. The instructions provided in a kit are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is evident from the above discussion that the above described invention provides methods and kits for treating a subject for a condition such as an inflammatory condition, a blood clotting condition, an adrenergic condition, and the like. In certain embodiments the subject methods may be employed to treat a plurality of conditions all at the same time using only one type of pharmacological agent, thereby simplifying treatment protocols and reducing treatment costs. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for osteoarthritis, said method comprising:
    (a) identifying said osteoarthritis; and
    (b) administering an effective amount of an autonomic nervous system modulator to said subject to treat said subject for said osteoarthritis, wherein said autonomic nervous system modulator is an antiadrenergic agent and said antiadrenergic agent is an angiotensin converting enzyme ("ACE") inhibitor.

2. A method of treating a subject for osteoarthritis, the method comprising pharmacologically modulating at least a portion of the autonomic nervous system of said subject to increase the parasympathetic activity/sympathetic activity ratio in a manner effective to treat said subject for said osteoarthritis, wherein said pharmacological modulation comprises administering an effective amount of an autonomic nervous system modulator and wherein said autonomic nervous system modulator is an angiotensin converting enzyme ("ACE") inhibitor.

* * * * *

UNITED STATES PATENT AND TRADEMARK OFFICE
CERTIFICATE OF CORRECTION

PATENT NO.         : 10,086,071 B2
APPLICATION NO.    : 14/035814
DATED              : October 2, 2018
INVENTOR(S)        : Anthony Joonkyoo Yun et al.

Page 1 of 1

It is certified that error appears in the above-identified patent and that said Letters Patent is hereby corrected as shown below:

In the Specification

Please replace "phenyloin" with -- "phenytoin" -- (Column 19, Line 16)

Please replace "fungi" with -- "hmg1" -- (Column 20, Line 46)

Please replace "phenyloin" with -- "phenytoin" -- (Column 25, Line 27)

Please replace "0.8" with -- "8" -- (Column 25, Line 39)

Please replace "N" with -- "IV" -- (Column 28, Line 23)

Signed and Sealed this
Eleventh Day of December, 2018

Andrei Iancu
*Director of the United States Patent and Trademark Office*